(12) United States Patent
Ruddenklau et al.

(10) Patent No.: US 11,090,103 B2
(45) Date of Patent: *Aug. 17, 2021

(54) MEDICAL DEVICE

(71) Applicant: Ethicon LLC, Guaynabo, PR (US)

(72) Inventors: David Ian Ruddenklau, Christchurch (NZ); Paul Christopher Roberts, Cambridge (GB); Alan Edward Green, Cambridge (GB)

(73) Assignee: Cilag GmbH International, Zug (CH)

( * ) Notice: Subject to any disclaimer, the term of this patent is extended or adjusted under 35 U.S.C. 154(b) by 1053 days.

This patent is subject to a terminal disclaimer.

(21) Appl. No.: 15/617,694

(22) Filed: Jun. 8, 2017

(65) Prior Publication Data

US 2017/0367751 A1 Dec. 28, 2017

Related U.S. Application Data

(62) Division of application No. 13/810,865, filed as application No. PCT/GB2011/000778 on May 20, 2011, now Pat. No. 9,707,027.

(30) Foreign Application Priority Data

May 21, 2010 (GB) ..................... 1008510

(51) Int. Cl.
*A61B 18/12* (2006.01)
*A61B 17/00* (2006.01)
(Continued)

(52) U.S. Cl.
CPC .......... *A61B 18/12* (2013.01); *A61B 18/1206* (2013.01); *A61B 2017/00734* (2013.01);
(Continued)

(58) Field of Classification Search
CPC . A61B 18/12; A61B 18/1206; A61B 2018/12; A61B 2018/1206;
(Continued)

(56) References Cited

U.S. PATENT DOCUMENTS 2,366,274 A 1/1945 Luth et al.
2,458,152 A 1/1949 Eakins
(Continued)

FOREIGN PATENT DOCUMENTS

CN 1634601 A 7/2005
CN 1922563 A 2/2007
(Continued)

OTHER PUBLICATIONS

Henriques. F.C., "Studies in thermal injury V. The predictability and the significance of thermally induced rate processes leading to irreversible epidermal injury." Archives of Pathology, 434, pp. 489-502 (1947).
(Continued)

*Primary Examiner* — Jaymi E Della

(57) ABSTRACT

A medical device is described having a handle and an end effector coupled to the handle. The end effector has at least one electrode for providing electrical signals to a tissue or vessel to be treated. An RF drive circuit is provided for generating an RF drive signal that is applied to the end effector electrode. The RF drive circuit includes a resonant circuit and a frequency controller is used to vary the frequency of a signal passed through the resonant circuit in order to control the power supplied to the end effector electrode.

4 Claims, 10 Drawing Sheets

(51) Int. Cl.
*A61B 18/00* (2006.01)
*A61B 18/14* (2006.01)

(52) U.S. Cl.
CPC ............... *A61B 2018/00595* (2013.01); *A61B 2018/00607* (2013.01); *A61B 2018/00642* (2013.01); *A61B 2018/00732* (2013.01); *A61B 2018/00827* (2013.01); *A61B 2018/00875* (2013.01); *A61B 2018/00892* (2013.01); *A61B 2018/1226* (2013.01); *A61B 2018/1452* (2013.01)

(58) Field of Classification Search
CPC .... A61B 2018/1226; A61B 2018/1286; A61B 2018/00595; A61B 2018/00875; A61B 2018/00732
See application file for complete search history.

(56) References Cited

U.S. PATENT DOCUMENTS

| | | |
|---|---|---|
| 2,510,693 A | 6/1950 | Green |
| 2,736,960 A | 3/1956 | Armstrong |
| 2,849,788 A | 9/1958 | Creek |
| 2,867,039 A | 1/1959 | Zach |
| 3,015,961 A | 1/1962 | Roney |
| 3,043,309 A | 7/1962 | McCarthy |
| 3,166,971 A | 1/1965 | Stoecker |
| 3,358,676 A | 12/1967 | Frei et al. |
| 3,525,912 A | 8/1970 | Wallin |
| 3,526,219 A | 9/1970 | Balamuth |
| 3,580,841 A | 5/1971 | Cadotte et al. |
| 3,614,484 A | 10/1971 | Shoh |
| 3,636,943 A | 1/1972 | Balamuth |
| 3,703,651 A | 11/1972 | Blowers |
| 3,710,399 A | 1/1973 | Hurst |
| 3,776,238 A | 12/1973 | Peyman et al. |
| 3,777,760 A | 12/1973 | Essner |
| 3,805,787 A | 4/1974 | Banko |
| 3,862,630 A | 1/1975 | Balamuth |
| 3,900,823 A | 8/1975 | Sokal et al. |
| 3,906,217 A | 9/1975 | Lackore |
| 3,918,442 A | 11/1975 | Nikolaev et al. |
| 3,946,738 A | 3/1976 | Newton et al. |
| 3,955,859 A | 5/1976 | Stella et al. |
| 3,956,826 A | 5/1976 | Perdreaux, Jr. |
| 3,988,535 A | 10/1976 | Hickman et al. |
| 4,005,714 A | 2/1977 | Hiltebrandt |
| 4,034,762 A | 7/1977 | Cosens et al. |
| 4,047,136 A | 9/1977 | Satto |
| 4,058,126 A | 11/1977 | Leveen |
| 4,063,561 A | 12/1977 | McKenna |
| 4,099,192 A | 7/1978 | Aizawa et al. |
| 4,156,187 A | 5/1979 | Murry et al. |
| 4,188,927 A | 2/1980 | Harris |
| 4,200,106 A | 4/1980 | Douvas et al. |
| 4,203,430 A | 5/1980 | Takahashi |
| 4,220,154 A | 9/1980 | Semm |
| 4,237,441 A | 12/1980 | van Konynenburg et al. |
| 4,278,077 A | 7/1981 | Mizumoto |
| 4,281,785 A | 8/1981 | Brooks |
| 4,304,987 A | 12/1981 | van Konynenburg |
| 4,314,559 A | 2/1982 | Allen |
| 4,384,584 A | 5/1983 | Chen |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,585,282 A | 4/1986 | Bosley |
| 4,597,390 A | 7/1986 | Mulhollan et al. |
| 4,617,927 A | 10/1986 | Manes |
| 4,633,874 A | 1/1987 | Chow et al. |
| 4,634,420 A | 1/1987 | Spinosa et al. |
| 4,640,279 A | 2/1987 | Beard |
| 4,655,746 A | 4/1987 | Daniels et al. |
| 4,671,287 A | 6/1987 | Fiddian-Green |
| 4,708,127 A | 11/1987 | Abdelghani |
| 4,735,603 A | 4/1988 | Goodson et al. |
| 4,761,871 A | 8/1988 | O'Connor et al. |
| 4,777,951 A | 10/1988 | Cribier et al. |
| 4,797,803 A | 1/1989 | Carroll |
| 4,798,588 A | 1/1989 | Aillon |
| 4,802,461 A | 2/1989 | Cho |
| 4,803,506 A | 2/1989 | Diehl et al. |
| 4,830,462 A | 5/1989 | Karny et al. |
| 4,832,683 A | 5/1989 | Idemoto et al. |
| 4,838,853 A | 6/1989 | Parisi |
| 4,849,133 A | 7/1989 | Yoshida et al. |
| 4,850,354 A | 7/1989 | McGurk-Burleson et al. |
| 4,860,745 A | 8/1989 | Farin et al. |
| 4,865,159 A | 9/1989 | Jamison |
| 4,878,493 A | 11/1989 | Pasternak et al. |
| 4,880,015 A | 11/1989 | Nierman |
| 4,896,009 A | 1/1990 | Pawlowski |
| 4,910,389 A | 3/1990 | Sherman et al. |
| 4,910,633 A | 3/1990 | Quinn |
| 4,911,148 A | 3/1990 | Sosnowski et al. |
| 4,919,129 A | 4/1990 | Weber, Jr. et al. |
| 4,920,978 A | 5/1990 | Colvin |
| 4,922,902 A | 5/1990 | Wuchinich et al. |
| 4,936,842 A | 6/1990 | D'Amelio et al. |
| 4,961,738 A | 10/1990 | Mackin |
| 4,967,670 A | 11/1990 | Morishita et al. |
| 4,981,756 A | 1/1991 | Rhandhawa |
| 5,007,919 A | 4/1991 | Silva et al. |
| 5,019,075 A | 5/1991 | Spears et al. |
| 5,020,514 A | 6/1991 | Heckele |
| 5,026,387 A | 6/1991 | Thomas |
| 5,061,269 A | 10/1991 | Muller |
| 5,093,754 A | 3/1992 | Kawashima |
| 5,099,216 A | 3/1992 | Pelrine |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,112,300 A | 5/1992 | Ureche |
| 5,123,903 A | 6/1992 | Quaid et al. |
| 5,150,102 A | 9/1992 | Takashima |
| 5,150,272 A | 9/1992 | Danley et al. |
| 5,156,633 A | 10/1992 | Smith |
| 5,160,334 A | 11/1992 | Billings et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |
| 5,184,605 A | 2/1993 | Grzeszykowski |
| 5,188,102 A | 2/1993 | Idemoto et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,217,460 A | 6/1993 | Knoepfler |
| 5,221,282 A | 6/1993 | Wuchinich |
| 5,226,910 A | 7/1993 | Kajiyama et al. |
| 5,234,428 A | 8/1993 | Kaufman |
| 5,241,236 A | 8/1993 | Sasaki et al. |
| 5,253,647 A | 10/1993 | Takahashi et al. |
| 5,254,130 A | 10/1993 | Poncet et al. |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,267,091 A | 11/1993 | Chen |
| 5,282,800 A | 2/1994 | Foshee et al. |
| 5,285,945 A | 2/1994 | Brinkerhoff et al. |
| 5,290,286 A | 3/1994 | Parins |
| 5,293,863 A | 3/1994 | Zhu et al. |

(56) References Cited

U.S. PATENT DOCUMENTS

| | | |
|---|---|---|
| 5,304,115 A | 4/1994 | Pflueger et al. |
| D347,474 S | 5/1994 | Olson |
| 5,309,927 A | 5/1994 | Welch |
| 5,312,023 A | 5/1994 | Green et al. |
| 5,313,306 A | 5/1994 | Kuban et al. |
| 5,318,563 A | 6/1994 | Malis et al. |
| 5,318,564 A | 6/1994 | Eggers |
| 5,318,565 A | 6/1994 | Kuriloff et al. |
| 5,318,570 A | 6/1994 | Hood et al. |
| 5,318,589 A | 6/1994 | Lichtman |
| 5,322,055 A | 6/1994 | Davison et al. |
| 5,324,260 A | 6/1994 | O'Neill et al. |
| 5,324,299 A | 6/1994 | Davison et al. |
| 5,326,013 A | 7/1994 | Green et al. |
| 5,330,471 A | 7/1994 | Eggers |
| 5,330,502 A | 7/1994 | Hassler et al. |
| 5,333,624 A | 8/1994 | Tovey |
| 5,339,723 A | 8/1994 | Huitema |
| 5,342,359 A | 8/1994 | Rydell |
| 5,344,420 A | 9/1994 | Hilal et al. |
| 5,346,502 A | 9/1994 | Estabrook et al. |
| 5,352,219 A | 10/1994 | Reddy |
| 5,359,992 A | 11/1994 | Hori et al. |
| 5,361,583 A | 11/1994 | Huitema |
| 5,366,466 A | 11/1994 | Christian et al. |
| 5,370,640 A | 12/1994 | Kolff |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,389,098 A | 2/1995 | Tsuruta et al. |
| 5,395,033 A | 3/1995 | Byrne et al. |
| 5,395,312 A | 3/1995 | Desai |
| 5,395,331 A | 3/1995 | O'Neill et al. |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,409,483 A | 4/1995 | Campbell et al. |
| D358,887 S | 5/1995 | Feinberg |
| 5,411,481 A | 5/1995 | Allen et al. |
| 5,413,575 A | 5/1995 | Haenggi |
| 5,417,709 A | 5/1995 | Slater |
| 5,419,761 A | 5/1995 | Narayanan et al. |
| 5,421,829 A | 6/1995 | Olichney et al. |
| 5,428,504 A | 6/1995 | Bhatla |
| 5,429,131 A | 7/1995 | Scheinman et al. |
| 5,431,640 A | 7/1995 | Gabriel |
| 5,443,463 A | 8/1995 | Stern et al. |
| 5,445,615 A | 8/1995 | Yoon |
| 5,445,638 A | 8/1995 | Rydell et al. |
| 5,449,370 A | 9/1995 | Vaitekunas |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,472,443 A | 12/1995 | Cordis et al. |
| 5,476,479 A | 12/1995 | Green et al. |
| 5,477,788 A | 12/1995 | Morishita |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,489,256 A | 2/1996 | Adair |
| 5,496,317 A | 3/1996 | Goble et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,648 A | 7/1996 | Yoon |
| 5,540,681 A | 7/1996 | Strul et al. |
| 5,542,916 A | 8/1996 | Hirsch et al. |
| 5,542,938 A | 8/1996 | Avellanet et al. |
| 5,558,671 A | 9/1996 | Yates |
| 5,562,609 A | 10/1996 | Brumbach |
| 5,562,610 A | 10/1996 | Brumbach |
| 5,562,657 A | 10/1996 | Griffin |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,601,601 A | 2/1997 | Tal et al. |
| 5,604,531 A | 2/1997 | Iddan et al. |
| 5,607,436 A | 3/1997 | Pratt et al. |
| 5,607,450 A | 3/1997 | Zvenyatsky et al. |
| 5,611,813 A | 3/1997 | Lichtman |
| 5,618,307 A | 4/1997 | Donlon et al. |
| 5,618,492 A | 4/1997 | Auten et al. |
| 5,624,452 A | 4/1997 | Yates |
| 5,626,578 A | 5/1997 | Tihon |
| 5,628,760 A | 5/1997 | Knoepfler |
| 5,630,420 A | 5/1997 | Vaitekunas |
| 5,632,432 A | 5/1997 | Schulze et al. |
| D381,077 S | 7/1997 | Hunt |
| 5,643,175 A | 7/1997 | Adair |
| 5,645,065 A | 7/1997 | Shapiro et al. |
| 5,647,871 A | 7/1997 | Levine et al. |
| 5,651,780 A | 7/1997 | Jackson et al. |
| 5,653,677 A | 8/1997 | Okada et al. |
| 5,653,713 A | 8/1997 | Michelson |
| 5,657,697 A | 8/1997 | Murai |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,681,260 A | 10/1997 | Ueda et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,700,243 A | 12/1997 | Narciso, Jr. |
| 5,700,261 A | 12/1997 | Brinkerhoff |
| 5,704,900 A | 1/1998 | Dobrovolny et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,722,326 A | 3/1998 | Post |
| 5,722,426 A | 3/1998 | Kolff |
| 5,732,636 A | 3/1998 | Wang et al. |
| 5,733,074 A | 3/1998 | Stock et al. |
| 5,735,848 A | 4/1998 | Yates et al. |
| 5,738,652 A | 4/1998 | Boyd et al. |
| 5,741,226 A | 4/1998 | Strukel et al. |
| 5,741,305 A | 4/1998 | Vincent et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,776,130 A | 7/1998 | Buysse et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |

(56) References Cited

U.S. PATENT DOCUMENTS

| | | | |
|---|---|---|---|
| 5,800,449 A | 9/1998 | Wales | |
| 5,805,140 A | 9/1998 | Rosenberg et al. | |
| 5,807,393 A | 9/1998 | Williamson, IV et al. | |
| 5,810,718 A | 9/1998 | Akiba et al. | |
| 5,810,811 A | 9/1998 | Yates et al. | |
| 5,810,859 A | 9/1998 | DiMatteo et al. | |
| 5,817,033 A | 10/1998 | DeSantis et al. | |
| 5,817,084 A | 10/1998 | Jensen | |
| 5,817,093 A | 10/1998 | Williamson, IV et al. | |
| 5,827,323 A | 10/1998 | Klieman et al. | |
| 5,828,160 A | 10/1998 | Sugishita | |
| 5,836,867 A | 11/1998 | Speier et al. | |
| 5,836,909 A | 11/1998 | Cosmescu | |
| 5,836,943 A * | 11/1998 | Miller, III | A61B 18/1206 606/34 |
| 5,836,990 A | 11/1998 | Li | |
| 5,843,109 A | 12/1998 | Mehta et al. | |
| 5,853,412 A | 12/1998 | Mayenberger | |
| 5,876,401 A | 3/1999 | Schulze et al. | |
| 5,878,193 A | 3/1999 | Wang et al. | |
| 5,879,364 A | 3/1999 | Bromfield et al. | |
| 5,880,668 A | 3/1999 | Hall | |
| 5,883,454 A | 3/1999 | Hones et al. | |
| 5,887,018 A | 3/1999 | Bayazitoglu et al. | |
| 5,891,142 A | 4/1999 | Eggers et al. | |
| 5,893,835 A | 4/1999 | Witt et al. | |
| 5,897,569 A | 4/1999 | Kellogg et al. | |
| 5,902,239 A | 5/1999 | Buurman | |
| 5,904,147 A | 5/1999 | Conlan et al. | |
| 5,906,579 A | 5/1999 | Vander Salm et al. | |
| 5,906,625 A | 5/1999 | Bito et al. | |
| 5,910,129 A | 6/1999 | Koblish et al. | |
| 5,921,956 A | 7/1999 | Grinberg et al. | |
| 5,929,846 A | 7/1999 | Rosenberg et al. | |
| 5,935,143 A | 8/1999 | Hood | |
| 5,935,144 A | 8/1999 | Estabrook | |
| 5,938,633 A | 8/1999 | Beaupre | |
| 5,944,298 A | 8/1999 | Koike | |
| 5,944,718 A | 8/1999 | Austin et al. | |
| 5,944,737 A | 8/1999 | Tsonton et al. | |
| 5,954,736 A | 9/1999 | Bishop et al. | |
| 5,954,746 A | 9/1999 | Holthaus et al. | |
| 5,957,849 A | 9/1999 | Munro | |
| 5,957,882 A | 9/1999 | Nita et al. | |
| 5,957,943 A | 9/1999 | Vaitekunas | |
| 5,968,007 A | 10/1999 | Simon et al. | |
| 5,968,060 A | 10/1999 | Kellogg | |
| D416,089 S | 11/1999 | Barton et al. | |
| 5,984,938 A | 11/1999 | Yoon | |
| 5,989,182 A | 11/1999 | Hori et al. | |
| 5,989,274 A | 11/1999 | Davison et al. | |
| 5,989,275 A | 11/1999 | Estabrook et al. | |
| 5,993,972 A | 11/1999 | Reich et al. | |
| 6,003,517 A | 12/1999 | Sheffield et al. | |
| 6,007,484 A | 12/1999 | Thompson | |
| 6,013,052 A | 1/2000 | Durman et al. | |
| 6,014,580 A | 1/2000 | Blume et al. | |
| 6,024,741 A | 2/2000 | Williamson, IV et al. | |
| 6,024,744 A | 2/2000 | Kese et al. | |
| 6,033,375 A | 3/2000 | Brumbach | |
| 6,033,399 A | 3/2000 | Gines | |
| 6,039,734 A | 3/2000 | Goble | |
| 6,050,996 A | 4/2000 | Schmaltz et al. | |
| 6,053,172 A | 4/2000 | Hovda et al. | |
| 6,063,098 A | 5/2000 | Houser et al. | |
| 6,066,132 A | 5/2000 | Chen et al. | |
| 6,068,629 A | 5/2000 | Haissaguerre et al. | |
| 6,068,647 A | 5/2000 | Witt et al. | |
| 6,074,389 A | 6/2000 | Levine et al. | |
| 6,077,285 A | 6/2000 | Boukhny | |
| 6,080,152 A | 6/2000 | Nardella et al. | |
| 6,083,151 A | 7/2000 | Renner et al. | |
| 6,083,191 A | 7/2000 | Rose | |
| 6,086,584 A | 7/2000 | Miller | |
| 6,090,120 A | 7/2000 | Wright et al. | |
| 6,091,995 A | 7/2000 | Ingle et al. | |
| 6,093,186 A * | 7/2000 | Goble | A61B 18/1206 606/32 |
| 6,099,483 A | 8/2000 | Palmer et al. | |
| 6,099,550 A | 8/2000 | Yoon | |
| 6,109,500 A | 8/2000 | Alli et al. | |
| 6,113,594 A | 9/2000 | Savage | |
| 6,113,598 A | 9/2000 | Baker | |
| 6,123,466 A | 9/2000 | Persson et al. | |
| H1904 H | 10/2000 | Yates et al. | |
| 6,127,757 A | 10/2000 | Swinbanks | |
| 6,132,368 A | 10/2000 | Cooper | |
| 6,139,320 A | 10/2000 | Hahn | |
| 6,144,402 A | 11/2000 | Norsworthy et al. | |
| 6,152,902 A | 11/2000 | Christian et al. | |
| 6,152,923 A | 11/2000 | Ryan | |
| 6,154,198 A | 11/2000 | Rosenberg | |
| 6,159,160 A | 12/2000 | Hsei et al. | |
| 6,159,175 A | 12/2000 | Strukel et al. | |
| 6,162,208 A | 12/2000 | Hipps | |
| 6,173,199 B1 | 1/2001 | Gabriel | |
| 6,173,715 B1 | 1/2001 | Sinanan et al. | |
| 6,174,309 B1 | 1/2001 | Wrublewski et al. | |
| 6,176,857 B1 | 1/2001 | Ashley | |
| 6,190,386 B1 | 2/2001 | Rydell | |
| 6,193,709 B1 | 2/2001 | Miyawaki et al. | |
| 6,206,844 B1 | 3/2001 | Reichel et al. | |
| 6,206,876 B1 | 3/2001 | Levine et al. | |
| 6,206,877 B1 | 3/2001 | Kese et al. | |
| 6,210,403 B1 | 4/2001 | Klicek | |
| 6,214,023 B1 | 4/2001 | Whipple et al. | |
| 6,219,572 B1 | 4/2001 | Young | |
| 6,221,007 B1 | 4/2001 | Green | |
| 6,228,080 B1 | 5/2001 | Gines | |
| 6,228,084 B1 | 5/2001 | Kirwan, Jr. | |
| 6,231,565 B1 | 5/2001 | Tovey et al. | |
| 6,233,476 B1 | 5/2001 | Strommer et al. | |
| 6,238,366 B1 | 5/2001 | Savage et al. | |
| 6,241,724 B1 | 6/2001 | Fleischman et al. | |
| 6,248,074 B1 | 6/2001 | Ohno et al. | |
| D444,365 S | 7/2001 | Bass et al. | |
| 6,254,623 B1 | 7/2001 | Haibel, Jr. et al. | |
| 6,258,034 B1 | 7/2001 | Hanafy | |
| 6,258,086 B1 | 7/2001 | Ashley et al. | |
| 6,259,230 B1 | 7/2001 | Chou | |
| 6,267,761 B1 | 7/2001 | Ryan | |
| 6,270,831 B2 | 8/2001 | Kumar et al. | |
| 6,273,852 B1 | 8/2001 | Lehe et al. | |
| 6,273,887 B1 | 8/2001 | Yamauchi et al. | |
| 6,274,963 B1 | 8/2001 | Estabrook et al. | |
| 6,277,115 B1 | 8/2001 | Saadat | |
| 6,277,117 B1 | 8/2001 | Tetzlaff et al. | |
| 6,278,218 B1 | 8/2001 | Madan et al. | |
| 6,283,981 B1 | 9/2001 | Beaupre | |
| 6,292,700 B1 | 9/2001 | Morrison et al. | |
| 6,309,400 B2 | 10/2001 | Beaupre | |
| 6,315,789 B1 | 11/2001 | Cragg | |
| 6,319,221 B1 | 11/2001 | Savage et al. | |
| 6,325,799 B1 | 12/2001 | Goble | |
| 6,325,811 B1 | 12/2001 | Messerly | |
| 6,328,751 B1 | 12/2001 | Beaupre | |
| 6,340,878 B1 | 1/2002 | Oglesbee | |
| 6,352,532 B1 | 3/2002 | Kramer et al. | |
| 6,364,888 B1 | 4/2002 | Niemeyer et al. | |
| 6,371,952 B1 | 4/2002 | Madhani et al. | |
| 6,379,320 B1 | 4/2002 | Lafon et al. | |
| 6,379,351 B1 | 4/2002 | Thapliyal et al. | |
| D457,958 S | 5/2002 | Dycus et al. | |
| 6,383,194 B1 | 5/2002 | Pothula | |
| 6,387,094 B1 | 5/2002 | Eitenmuller | |
| 6,387,109 B1 | 5/2002 | Davison et al. | |
| 6,388,657 B1 | 5/2002 | Natoli | |
| 6,391,026 B1 | 5/2002 | Hung et al. | |
| 6,391,042 B1 | 5/2002 | Cimino | |
| 6,398,779 B1 | 6/2002 | Buysse et al. | |
| 6,409,722 B1 | 6/2002 | Hoey et al. | |
| H2037 H | 7/2002 | Yates et al. | |
| 6,416,469 B1 | 7/2002 | Phung et al. | |
| 6,416,486 B1 | 7/2002 | Wampler | |

(56) References Cited

U.S. PATENT DOCUMENTS

| | | |
|---|---|---|
| 6,419,675 B1 | 7/2002 | Gallo, Sr. |
| 6,423,073 B2 | 7/2002 | Bowman |
| 6,423,082 B1 | 7/2002 | Houser et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,443,968 B1 | 9/2002 | Holthaus et al. |
| 6,443,969 B1 | 9/2002 | Novak et al. |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,464,703 B2 | 10/2002 | Bartel |
| 6,471,172 B1 | 10/2002 | Lemke et al. |
| 6,475,211 B2 | 11/2002 | Chess et al. |
| 6,475,216 B2 | 11/2002 | Mulier et al. |
| 6,480,796 B2 | 11/2002 | Wiener |
| 6,485,490 B2 | 11/2002 | Wampler et al. |
| 6,491,690 B1 | 12/2002 | Goble et al. |
| 6,491,691 B1 | 12/2002 | Morley et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,503,248 B1 | 1/2003 | Levine |
| 6,506,208 B2 | 1/2003 | Hunt et al. |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,520,960 B2 | 2/2003 | Blocher et al. |
| 6,522,909 B1 | 2/2003 | Garibaldi et al. |
| 6,524,316 B1 | 2/2003 | Nicholson et al. |
| 6,531,846 B1 | 3/2003 | Smith |
| 6,533,784 B2 | 3/2003 | Truckai et al. |
| 6,537,196 B1 | 3/2003 | Creighton, IV et al. |
| 6,537,272 B2 | 3/2003 | Christopherson et al. |
| 6,537,291 B2 | 3/2003 | Friedman et al. |
| 6,540,693 B2 | 4/2003 | Burbank et al. |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,037 B2 | 5/2003 | Paton et al. |
| 6,572,632 B2 | 6/2003 | Zisterer et al. |
| 6,572,639 B2 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,589,239 B2 | 7/2003 | Khandkar et al. |
| 6,594,517 B1 | 7/2003 | Nevo |
| 6,599,321 B2 | 7/2003 | Hyde, Jr. |
| 6,602,252 B2 | 8/2003 | Mollenauer |
| 6,610,060 B2 | 8/2003 | Mulier et al. |
| 6,616,450 B2 | 9/2003 | Mossle et al. |
| 6,616,600 B2 | 9/2003 | Pauker |
| 6,619,529 B2 | 9/2003 | Green et al. |
| 6,620,129 B2 | 9/2003 | Stecker et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,817 B2 | 11/2003 | Schara et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,663,941 B2 | 12/2003 | Brown et al. |
| 6,669,690 B1 | 12/2003 | Okada et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,695,840 B2 | 2/2004 | Schulze |
| 6,716,215 B1 | 4/2004 | David et al. |
| 6,719,684 B2 | 4/2004 | Kim et al. |
| 6,719,765 B2 | 4/2004 | Bonutti |
| 6,722,552 B2 | 4/2004 | Fenton, Jr. |
| 6,726,686 B2 | 4/2004 | Buysse et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,743,229 B2 | 6/2004 | Buysse et al. |
| 6,746,443 B1 | 6/2004 | Morley et al. |
| 6,752,815 B2 | 6/2004 | Beaupre |
| 6,762,535 B2 | 7/2004 | Take et al. |
| 6,766,202 B2 | 7/2004 | Underwood et al. |
| 6,767,349 B2 | 7/2004 | Ouchi |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,165 B2 | 8/2004 | Jin |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,216 B1 | 9/2004 | Ishikawa |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,806,317 B2 | 10/2004 | Morishita et al. |
| 6,808,491 B2 | 10/2004 | Kortenbach et al. |
| 6,811,842 B1 | 11/2004 | Ehrnsperger et al. |
| 6,814,731 B2 | 11/2004 | Swanson |
| 6,817,974 B2 | 11/2004 | Cooper et al. |
| 6,821,273 B2 | 11/2004 | Mollenauer |
| 6,828,712 B2 | 12/2004 | Battaglin et al. |
| 6,832,998 B2 | 12/2004 | Goble |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,869,439 B2 | 3/2005 | White et al. |
| 6,875,220 B2 | 4/2005 | Du et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,632 B2 | 8/2005 | Nita et al. |
| 6,929,644 B2 | 8/2005 | Truckai et al. |
| 6,936,003 B2 | 8/2005 | Iddan |
| D509,589 S | 9/2005 | Wells |
| 6,939,347 B2 | 9/2005 | Thompson |
| 6,945,981 B2 | 9/2005 | Donofrio et al. |
| 6,953,461 B2 | 10/2005 | McClurken et al. |
| D511,145 S | 11/2005 | Donofrio et al. |
| 6,959,852 B2 | 11/2005 | Shelton, IV et al. |
| 6,974,462 B2 | 12/2005 | Sater |
| 6,976,844 B2 | 12/2005 | Hickok et al. |

(56) References Cited

U.S. PATENT DOCUMENTS

| | | |
|---|---|---|
| 6,976,969 B2 | 12/2005 | Messerly |
| 6,977,495 B2 | 12/2005 | Donofrio |
| 6,984,220 B2 | 1/2006 | Wuchinich |
| 6,986,738 B2 | 1/2006 | Glukhovsky et al. |
| 6,986,780 B2 | 1/2006 | Rudnick et al. |
| 6,994,709 B2 | 2/2006 | Iida |
| 7,000,818 B2 | 2/2006 | Shelton, IV et al. |
| 7,004,951 B2 | 2/2006 | Gibbens, III |
| 7,011,657 B2 | 3/2006 | Truckai et al. |
| 7,029,435 B2 | 4/2006 | Nakao |
| 7,039,453 B2 | 5/2006 | Mullick et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,352 B2 | 5/2006 | Shelton, IV et al. |
| 7,044,937 B1 | 5/2006 | Kirwan et al. |
| 7,052,496 B2 | 5/2006 | Yamauchi |
| 7,055,731 B2 | 6/2006 | Shelton, IV et al. |
| 7,056,284 B2 | 6/2006 | Martone et al. |
| 7,063,699 B2 | 6/2006 | Hess et al. |
| 7,066,879 B2 | 6/2006 | Fowler et al. |
| 7,066,936 B2 | 6/2006 | Ryan |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,579 B2 | 8/2006 | Yokoi et al. |
| 7,083,617 B2 | 8/2006 | Kortenbach et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,094,235 B2 | 8/2006 | Francischelli |
| 7,096,560 B2 | 8/2006 | Oddsen, Jr. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,118,570 B2 | 10/2006 | Tetzlaff et al. |
| 7,120,498 B2 | 10/2006 | Imran et al. |
| 7,124,932 B2 | 10/2006 | Isaacson et al. |
| 7,125,409 B2 | 10/2006 | Truckai et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,147,638 B2 | 12/2006 | Chapman et al. |
| 7,153,315 B2 | 12/2006 | Miller |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,298 B2 | 1/2007 | Lawes et al. |
| 7,163,548 B2 | 1/2007 | Stulen et al. |
| 7,169,104 B2 | 1/2007 | Ueda et al. |
| 7,169,146 B2 | 1/2007 | Truckai et al. |
| 7,169,156 B2 | 1/2007 | Hart |
| 7,170,823 B2 | 1/2007 | Fabricius et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,199,545 B2 | 4/2007 | Oleynikov et al. |
| 7,204,820 B2 | 4/2007 | Akahoshi |
| 7,207,471 B2 | 4/2007 | Heinrich et al. |
| 7,208,005 B2 | 4/2007 | Frecker et al. |
| 7,211,094 B2 | 5/2007 | Gannoe et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,064 B2 | 6/2007 | Hopper et al. |
| 7,235,073 B2 | 6/2007 | Levine et al. |
| 7,241,290 B2 | 7/2007 | Doyle et al. |
| 7,241,294 B2 | 7/2007 | Reschke |
| 7,241,296 B2 | 7/2007 | Buysse et al. |
| 7,246,734 B2 | 7/2007 | Shelton, IV |
| 7,251,531 B2 | 7/2007 | Mosher et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,267,685 B2 | 9/2007 | Butaric et al. |
| 7,270,658 B2 | 9/2007 | Woloszko et al. |
| 7,270,664 B2 | 9/2007 | Johnson et al. |
| 7,273,483 B2 | 9/2007 | Wiener et al. |
| 7,276,065 B2 | 10/2007 | Morley et al. |
| 7,282,773 B2 | 10/2007 | Li et al. |
| 7,287,682 B1 | 10/2007 | Ezzat et al. |
| 7,297,145 B2 | 11/2007 | Woloszko et al. |
| 7,297,149 B2 | 11/2007 | Vitali et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,360,542 B2 | 4/2008 | Nelson et al. |
| 7,364,577 B2 | 4/2008 | Wham et al. |
| 7,367,973 B2 | 5/2008 | Manzo et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,416,101 B2 | 8/2008 | Shelton, IV et al. |
| D576,725 S | 9/2008 | Shumer et al. |
| 7,422,139 B2 | 9/2008 | Shelton, IV et al. |
| 7,422,586 B2 | 9/2008 | Morris et al. |
| 7,422,592 B2 | 9/2008 | Morley et al. |
| 7,429,259 B2 | 9/2008 | Cadeddu et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,435,249 B2 | 10/2008 | Buysse et al. |
| 7,435,582 B2 | 10/2008 | Zimmermann et al. |
| 7,439,732 B2 | 10/2008 | LaPlaca |
| 7,441,684 B2 | 10/2008 | Shelton, IV et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,448,993 B2 | 11/2008 | Yokoi et al. |
| 7,449,004 B2 | 11/2008 | Yamada et al. |
| 7,450,998 B2 | 11/2008 | Zilberman et al. |
| 7,451,904 B2 | 11/2008 | Shelton, IV |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,479,148 B2 | 1/2009 | Beaupre |
| 7,479,160 B2 | 1/2009 | Branch et al. |
| 7,487,899 B2 | 2/2009 | Shelton, IV et al. |

(56) References Cited

U.S. PATENT DOCUMENTS

| | | |
|---|---|---|
| 7,488,319 B2 | 2/2009 | Yates |
| 7,491,201 B2 | 2/2009 | Shields et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,503,893 B2 | 3/2009 | Kucklick |
| 7,505,812 B1 | 3/2009 | Eggers et al. |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,511,733 B2 | 3/2009 | Takizawa et al. |
| 7,513,025 B2 | 4/2009 | Fischer |
| 7,517,349 B2 | 4/2009 | Truckai et al. |
| 7,520,877 B2 | 4/2009 | Lee, Jr. et al. |
| 7,524,320 B2 | 4/2009 | Tierney et al. |
| 7,534,243 B1 | 5/2009 | Chin et al. |
| D594,983 S | 6/2009 | Price et al. |
| 7,540,872 B2 | 6/2009 | Schechter et al. |
| 7,543,730 B1 | 6/2009 | Marczyk |
| 7,544,200 B2 | 6/2009 | Houser |
| 7,550,216 B2 | 6/2009 | Ofer et al. |
| 7,553,309 B2 | 6/2009 | Buysse et al. |
| 7,559,452 B2 | 7/2009 | Wales et al. |
| 7,566,318 B2 | 7/2009 | Haefner |
| 7,567,012 B2 | 7/2009 | Namikawa |
| 7,582,086 B2 | 9/2009 | Privitera et al. |
| 7,582,087 B2 | 9/2009 | Tetzlaff et al. |
| 7,586,289 B2 | 9/2009 | Andruk et al. |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,599,743 B2 | 10/2009 | Hassler, Jr. et al. |
| 7,601,119 B2 | 10/2009 | Shahinian |
| 7,604,150 B2 | 10/2009 | Boudreaux |
| 7,611,512 B2 | 11/2009 | Ein-Gal |
| 7,617,961 B2 | 11/2009 | Viola |
| 7,621,910 B2 | 11/2009 | Sugi |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,640,447 B2 | 12/2009 | Qiu |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,678,043 B2 | 3/2010 | Gilad |
| 7,678,105 B2 | 3/2010 | McGreevy et al. |
| 7,686,804 B2 | 3/2010 | Johnson et al. |
| 7,691,095 B2 | 4/2010 | Bednarek et al. |
| 7,691,098 B2 | 4/2010 | Wallace et al. |
| 7,691,103 B2 | 4/2010 | Fernandez et al. |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,717,312 B2 | 5/2010 | Beetel |
| 7,717,914 B2 | 5/2010 | Kimura |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,725,214 B2 | 5/2010 | Diolaiti |
| D618,797 S | 6/2010 | Price et al. |
| 7,726,537 B2 | 6/2010 | Olson et al. |
| 7,744,615 B2 | 6/2010 | Couture |
| 7,751,115 B2 | 7/2010 | Song |
| 7,753,904 B2 | 7/2010 | Shelton, IV et al. |
| 7,753,908 B2 | 7/2010 | Swanson |
| 7,753,909 B2 | 7/2010 | Chapman et al. |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,775,972 B2 | 8/2010 | Brock et al. |
| 7,776,036 B2 | 8/2010 | Schechter et al. |
| 7,776,037 B2 | 8/2010 | Odom |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,663 B2 | 8/2010 | Shelton, IV |
| 7,789,283 B2 | 9/2010 | Shah |
| 7,789,878 B2 | 9/2010 | Dumbauld et al. |
| 7,789,883 B2 | 9/2010 | Takashino et al. |
| 7,793,814 B2 | 9/2010 | Racenet et al. |
| 7,799,027 B2 | 9/2010 | Hafner |
| 7,803,156 B2 | 9/2010 | Eder et al. |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| D627,066 S | 11/2010 | Romero |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,837,699 B2 | 11/2010 | Yamada et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,850,688 B2 | 12/2010 | Hafner |
| D631,155 S | 1/2011 | Peine et al. |
| 7,861,906 B2 | 1/2011 | Doll et al. |
| 7,862,560 B2 | 1/2011 | Marion |
| 7,867,228 B2 | 1/2011 | Nobis et al. |
| 7,871,392 B2 | 1/2011 | Sartor |
| 7,871,423 B2 | 1/2011 | Livneh |
| D631,965 S | 2/2011 | Price et al. |
| 7,877,852 B2 | 2/2011 | Unger et al. |
| 7,877,853 B2 | 2/2011 | Unger et al. |
| 7,879,035 B2 | 2/2011 | Garrison et al. |
| 7,879,070 B2 | 2/2011 | Ortiz et al. |
| 7,887,535 B2 | 2/2011 | Lands et al. |
| 7,892,606 B2 | 2/2011 | Thies et al. |
| 7,896,875 B2 | 3/2011 | Heim et al. |
| 7,896,878 B2 | 3/2011 | Johnson et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,922,953 B2 | 4/2011 | Guerra |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,942,303 B2 | 5/2011 | Shah |
| 7,942,868 B2 | 5/2011 | Cooper |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,976,544 B2 | 7/2011 | McClurken et al. |
| 7,980,443 B2 | 7/2011 | Scheib et al. |
| 7,981,113 B2 | 7/2011 | Truckai et al. |
| 7,988,567 B2 | 8/2011 | Kim et al. |

(56) References Cited

U.S. PATENT DOCUMENTS

| | | |
|---|---|---|
| 7,997,278 B2 | 8/2011 | Utley et al. |
| 8,020,743 B2 | 9/2011 | Shelton, IV |
| 8,033,173 B2 | 10/2011 | Ehlert et al. |
| 8,038,612 B2 | 10/2011 | Paz |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,056,787 B2 | 11/2011 | Boudreaux et al. |
| 8,057,498 B2 | 11/2011 | Robertson |
| 8,058,771 B2 | 11/2011 | Giordano et al. |
| 8,061,014 B2 | 11/2011 | Smith et al. |
| 8,062,211 B2 | 11/2011 | Duval et al. |
| 8,066,167 B2 | 11/2011 | Measamer et al. |
| 8,070,036 B1 | 12/2011 | Knodel |
| 8,070,748 B2 | 12/2011 | Hixson et al. |
| 8,075,555 B2 | 12/2011 | Truckai et al. |
| 8,075,558 B2 | 12/2011 | Truckai et al. |
| 8,092,475 B2 | 1/2012 | Cotter et al. |
| 8,100,894 B2 | 1/2012 | Mucko et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,114,119 B2 | 2/2012 | Spivey et al. |
| 8,128,624 B2 | 3/2012 | Couture et al. |
| 8,128,657 B2 | 3/2012 | Shiono et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,461 B2 | 3/2012 | Houser et al. |
| 8,147,488 B2 | 4/2012 | Masuda |
| 8,147,508 B2 | 4/2012 | Madan et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,940 B2 | 4/2012 | Johnson et al. |
| 8,177,794 B2 | 5/2012 | Cabrera et al. |
| 8,182,502 B2 | 5/2012 | Stulen et al. |
| 8,186,560 B2 | 5/2012 | Hess et al. |
| 8,187,166 B2 | 5/2012 | Kuth et al. |
| 8,187,267 B2 | 5/2012 | Pappone et al. |
| 8,192,433 B2 | 6/2012 | Johnson et al. |
| 8,197,472 B2 | 6/2012 | Lau et al. |
| 8,197,479 B2 | 6/2012 | Olson et al. |
| 8,197,494 B2 | 6/2012 | Jaggi et al. |
| 8,197,502 B2 | 6/2012 | Smith et al. |
| 8,206,212 B2 | 6/2012 | Iddings et al. |
| 8,221,415 B2 | 7/2012 | Francischelli |
| 8,221,416 B2 | 7/2012 | Townsend |
| 8,226,675 B2 | 7/2012 | Houser et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,244,368 B2 | 8/2012 | Sherman |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,252,012 B2 | 8/2012 | Stulen |
| 8,257,352 B2 | 9/2012 | Lawes et al. |
| 8,257,377 B2 | 9/2012 | Wiener et al. |
| 8,262,563 B2 | 9/2012 | Bakos et al. |
| 8,267,300 B2 | 9/2012 | Boudreaux |
| 8,267,854 B2 | 9/2012 | Asada et al. |
| 8,267,935 B2 | 9/2012 | Couture et al. |
| 8,273,085 B2 | 9/2012 | Park et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,292,888 B2 | 10/2012 | Whitman |
| 8,298,228 B2 | 10/2012 | Buysse et al. |
| 8,298,232 B2 | 10/2012 | Unger |
| 8,303,583 B2 | 11/2012 | Hosier et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,322,455 B2 | 12/2012 | Shelton, IV et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,158 B2 | 1/2013 | McKenna et al. |
| 8,361,569 B2 | 1/2013 | Saito et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,053 B2 | 2/2013 | Orszulak |
| 8,377,059 B2 | 2/2013 | Deville et al. |
| 8,377,085 B2 | 2/2013 | Smith et al. |
| 8,382,754 B2 | 2/2013 | Odom et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,094 B2 | 3/2013 | Edwards et al. |
| 8,394,115 B2 | 3/2013 | Houser et al. |
| 8,397,971 B2 | 3/2013 | Yates et al. |
| 8,398,633 B2 | 3/2013 | Mueller |
| 8,403,926 B2 | 3/2013 | Nobis et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,076 B2 | 4/2013 | Pang et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,911 B2 | 5/2013 | Mueller |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,956 B2 | 6/2013 | McKenna et al. |
| 8,469,981 B2 | 6/2013 | Robertson et al. |
| 8,475,361 B2 | 7/2013 | Barlow et al. |
| 8,475,453 B2 | 7/2013 | Marczyk et al. |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,625 B2 | 7/2013 | Horner |

(56) References Cited

U.S. PATENT DOCUMENTS

| | | | |
|---|---|---|---|
| 8,496,682 B2 | 7/2013 | Guerra et al. |
| 8,512,336 B2 | 8/2013 | Couture |
| 8,512,364 B2 | 8/2013 | Kowalski et al. |
| 8,512,365 B2 | 8/2013 | Wiener et al. |
| 8,523,889 B2 | 9/2013 | Stulen et al. |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,542,501 B2 | 9/2013 | Kyono |
| 8,553,430 B2 | 10/2013 | Melanson et al. |
| 8,562,516 B2 | 10/2013 | Saadat et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,187 B2 | 11/2013 | Marion |
| 8,574,231 B2 | 11/2013 | Boudreaux et al. |
| 8,579,176 B2 | 11/2013 | Smith et al. |
| 8,579,928 B2 | 11/2013 | Robertson et al. |
| 8,579,937 B2 | 11/2013 | Gresham |
| 8,591,459 B2 | 11/2013 | Clymer et al. |
| 8,591,506 B2 | 11/2013 | Wham et al. |
| D695,407 S | 12/2013 | Price et al. |
| 8,596,513 B2 | 12/2013 | Olson et al. |
| 8,597,182 B2 | 12/2013 | Stein et al. |
| 8,597,297 B2 | 12/2013 | Couture et al. |
| 8,608,044 B2 | 12/2013 | Hueil et al. |
| 8,613,383 B2 | 12/2013 | Beckman et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,632,539 B2 | 1/2014 | Twomey et al. |
| 8,636,648 B2 | 1/2014 | Gazdzinski |
| 8,636,736 B2 | 1/2014 | Yates et al. |
| 8,636,761 B2 | 1/2014 | Cunningham et al. |
| 8,638,428 B2 | 1/2014 | Brown |
| 8,640,788 B2 | 2/2014 | Dachs, II et al. |
| 8,641,712 B2 | 2/2014 | Couture |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,155 B2 | 2/2014 | Houser et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,668,691 B2 | 3/2014 | Heard |
| RE44,834 E | 4/2014 | Dumbauld et al. |
| 8,684,253 B2 | 4/2014 | Giordano et al. |
| 8,685,020 B2 | 4/2014 | Weizman et al. |
| 8,685,056 B2 | 4/2014 | Evans et al. |
| 8,696,662 B2 | 4/2014 | Eder et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,708,213 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,758,342 B2 | 6/2014 | Bales et al. |
| 8,764,747 B2 | 7/2014 | Cummings et al. |
| 8,770,459 B2 | 7/2014 | Racenet et al. |
| 8,784,418 B2 | 7/2014 | Romero |
| 8,789,740 B2 | 7/2014 | Baxter, III et al. |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,752 B2 | 8/2014 | Fortier et al. |
| 8,807,414 B2 | 8/2014 | Ross et al. |
| 8,808,319 B2 | 8/2014 | Houser et al. |
| 8,814,856 B2 | 8/2014 | Elmouelhi et al. |
| 8,814,865 B2 | 8/2014 | Reschke |
| 8,814,870 B2 | 8/2014 | Paraschiv et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,488 B2 | 9/2014 | Farritor et al. |
| 8,834,518 B2 | 9/2014 | Faller et al. |
| 8,845,630 B2 | 9/2014 | Mehta et al. |
| 8,851,354 B2 | 10/2014 | Swensgard et al. |
| 8,852,184 B2 | 10/2014 | Kucklick |
| 8,864,757 B2 | 10/2014 | Klimovitch et al. |
| 8,864,761 B2 | 10/2014 | Johnson et al. |
| 8,870,867 B2 | 10/2014 | Walberg et al. |
| 8,876,858 B2 | 11/2014 | Braun |
| 8,882,766 B2 | 11/2014 | Couture et al. |
| 8,882,791 B2 | 11/2014 | Stulen |
| 8,887,373 B2 | 11/2014 | Brandt et al. |
| 8,888,776 B2 | 11/2014 | Dietz et al. |
| 8,888,783 B2 | 11/2014 | Young |
| 8,888,809 B2 | 11/2014 | Davison et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,926,607 B2 | 1/2015 | Norvell et al. |
| 8,926,608 B2 | 1/2015 | Bacher et al. |
| 8,929,888 B2 | 1/2015 | Rao et al. |
| 8,931,682 B2 | 1/2015 | Timm et al. |
| 8,939,287 B2 | 1/2015 | Markovitch |
| 8,939,974 B2 | 1/2015 | Boudreaux et al. |
| 8,939,975 B2 | 1/2015 | Twomey et al. |
| 8,944,997 B2 | 2/2015 | Fernandez et al. |
| 8,945,125 B2 | 2/2015 | Schechter et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,968,276 B2 | 3/2015 | Zemlok et al. |
| 8,968,308 B2 | 3/2015 | Horner et al. |
| 8,968,312 B2 | 3/2015 | Marczyk et al. |
| 8,968,332 B2 | 3/2015 | Farritor et al. |
| 8,978,845 B2 | 3/2015 | Kim |
| 8,979,838 B2 | 3/2015 | Woloszko et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,989,855 B2 | 3/2015 | Murphy et al. |
| 8,992,422 B2 | 3/2015 | Spivey et al. |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,017,326 B2 | 4/2015 | DiNardo et al. |
| 9,017,372 B2 | 4/2015 | Artale et al. |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,983 B2 | 5/2015 | Takashino et al. |
| 9,039,695 B2 | 5/2015 | Giordano et al. |
| 9,039,705 B2 | 5/2015 | Takashino |
| 9,039,731 B2 | 5/2015 | Joseph |
| 9,044,227 B2 | 6/2015 | Shelton, IV et al. |

(56) References Cited

U.S. PATENT DOCUMENTS

| | | |
|---|---|---|
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,113 B2 | 6/2015 | Bloom et al. |
| 9,055,961 B2 | 6/2015 | Manzo et al. |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,078,664 B2 | 7/2015 | Palmer et al. |
| 9,089,327 B2 | 7/2015 | Worrell et al. |
| 9,089,360 B2 | 7/2015 | Messerly et al. |
| 9,094,006 B2 | 7/2015 | Gravati et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,672 B2 | 8/2015 | Tetzlaff et al. |
| 9,113,889 B2 | 8/2015 | Reschke |
| 9,113,900 B2 | 8/2015 | Buysse et al. |
| 9,119,630 B2 | 9/2015 | Townsend et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,138,289 B2 | 9/2015 | Conley et al. |
| 9,149,324 B2 | 10/2015 | Huang et al. |
| 9,149,325 B2 | 10/2015 | Worrell et al. |
| 9,155,585 B2 | 10/2015 | Bales, Jr. et al. |
| 9,161,803 B2 | 10/2015 | Yates et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,179,912 B2 | 11/2015 | Yates et al. |
| 9,186,204 B2 | 11/2015 | Nishimura et al. |
| 9,187,758 B2 | 11/2015 | Cai et al. |
| 9,192,380 B2 | 11/2015 | (Tarinelli) Racenet et al. |
| 9,192,421 B2 | 11/2015 | Garrison |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,716 B2 | 12/2015 | Masuda et al. |
| 9,204,879 B2 | 12/2015 | Shelton, IV |
| 9,204,919 B2 | 12/2015 | Brandt et al. |
| 9,216,050 B2 | 12/2015 | Condie et al. |
| 9,220,559 B2 | 12/2015 | Worrell et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,571 B2 | 2/2016 | Twomey et al. |
| 9,265,926 B2 | 2/2016 | Strobl et al. |
| 9,271,784 B2 | 3/2016 | Evans et al. |
| 9,274,988 B2 | 3/2016 | Hsu et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,308,014 B2 | 4/2016 | Fischer |
| 9,314,292 B2 | 4/2016 | Trees et al. |
| 9,326,788 B2 | 5/2016 | Batross et al. |
| 9,326,812 B2 | 5/2016 | Waaler et al. |
| 9,333,025 B2 | 5/2016 | Monson et al. |
| 9,339,323 B2 | 5/2016 | Eder et al. |
| 9,339,326 B2 | 5/2016 | McCullagh et al. |
| 9,344,042 B2 | 5/2016 | Mao |
| 9,345,481 B2 | 5/2016 | Hall et al. |
| 9,345,900 B2 | 5/2016 | Wu et al. |
| 9,351,754 B2 | 5/2016 | Vakharia et al. |
| 9,358,065 B2 | 6/2016 | Ladtkow et al. |
| 9,364,225 B2 | 6/2016 | Sniffin et al. |
| 9,364,230 B2 | 6/2016 | Shelton, IV et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,381,060 B2 | 7/2016 | Artale et al. |
| 9,386,983 B2 | 7/2016 | Swensgard et al. |
| 9,393,037 B2 | 7/2016 | Olson et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,456,876 B2 | 10/2016 | Hagn |
| 9,468,490 B2 | 10/2016 | Twomey et al. |
| 9,492,224 B2 | 11/2016 | Boudreaux et al. |
| 9,504,524 B2 | 11/2016 | Behnke, II |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,549,663 B2 | 1/2017 | Larkin |
| 9,554,845 B2 | 1/2017 | Arts |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,585,709 B2 | 3/2017 | Krapohl |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,810 B2 | 4/2017 | Hart et al. |
| 9,627,120 B2 | 4/2017 | Scott et al. |
| 9,629,629 B2 | 4/2017 | Leimbach et al. |
| 9,642,669 B2 | 5/2017 | Takashino et al. |
| 9,649,111 B2 | 5/2017 | Shelton, IV et al. |
| 9,649,144 B2 | 5/2017 | Aluru et al. |
| 9,649,151 B2 | 5/2017 | Goodman et al. |
| 9,662,131 B2 | 5/2017 | Omori et al. |
| 9,668,806 B2 | 6/2017 | Unger et al. |
| 9,687,295 B2 | 6/2017 | Joseph |
| 9,700,339 B2 | 7/2017 | Nield |
| 9,707,005 B2 | 7/2017 | Strobl et al. |
| 9,707,027 B2 | 7/2017 | Ruddenklau et al. |
| 9,707,030 B2 | 7/2017 | Davison et al. |
| 9,713,489 B2 | 7/2017 | Woloszko et al. |
| 9,713,491 B2 | 7/2017 | Roy et al. |
| 9,724,118 B2 | 8/2017 | Schulte et al. |
| 9,724,152 B2 | 8/2017 | Horlle et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,757,128 B2 | 9/2017 | Baber et al. |
| 9,757,142 B2 | 9/2017 | Shimizu |
| 9,757,186 B2 | 9/2017 | Boudreaux et al. |
| 9,782,214 B2 | 10/2017 | Houser et al. |
| 9,782,220 B2 | 10/2017 | Mark et al. |
| 9,795,436 B2 | 10/2017 | Yates et al. |
| 9,802,033 B2 | 10/2017 | Hibner et al. |
| 9,808,244 B2 | 11/2017 | Leimbach et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,833,239 B2 | 12/2017 | Yates et al. |
| 9,848,937 B2 | 12/2017 | Trees et al. |
| 9,848,939 B2 | 12/2017 | Mayer et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |

(56) References Cited

U.S. PATENT DOCUMENTS

| | | |
|---|---|---|
| 9,877,782 B2 | 1/2018 | Voegele et al. |
| 9,888,958 B2 | 2/2018 | Evans et al. |
| 9,901,390 B2 | 2/2018 | Allen, IV et al. |
| 9,901,754 B2 | 2/2018 | Yamada |
| 9,907,563 B2 | 3/2018 | Germain et al. |
| 9,913,680 B2 | 3/2018 | Voegele et al. |
| 9,918,730 B2 | 3/2018 | Trees et al. |
| 9,918,773 B2 | 3/2018 | Ishikawa et al. |
| 9,931,157 B2 | 4/2018 | Strobl et al. |
| 9,937,001 B2 | 4/2018 | Nakamura |
| 9,943,357 B2 | 4/2018 | Cunningham et al. |
| 9,949,620 B2 | 4/2018 | Duval et al. |
| 9,949,785 B2 | 4/2018 | Price et al. |
| 9,949,788 B2 | 4/2018 | Boudreaux |
| 9,974,539 B2 | 5/2018 | Yates et al. |
| 9,993,289 B2 | 6/2018 | Sobajima et al. |
| 10,010,339 B2 | 7/2018 | Witt et al. |
| 10,016,207 B2 | 7/2018 | Suzuki et al. |
| 10,022,142 B2 | 7/2018 | Aranyi et al. |
| 10,034,707 B2 | 7/2018 | Papaioannou et al. |
| 10,041,822 B2 | 8/2018 | Zemlok |
| 10,052,044 B2 | 8/2018 | Shelton, IV et al. |
| 10,058,376 B2 | 8/2018 | Horner et al. |
| 10,070,916 B2 | 9/2018 | Artale |
| 10,080,606 B2 | 9/2018 | Kappus et al. |
| 10,092,310 B2 | 10/2018 | Boudreaux et al. |
| 10,092,348 B2 | 10/2018 | Boudreaux |
| 10,092,350 B2 | 10/2018 | Rothweiler et al. |
| 10,105,174 B2 | 10/2018 | Krapohl |
| 10,111,699 B2 | 10/2018 | Boudreaux |
| 10,117,702 B2 | 11/2018 | Danziger et al. |
| 10,130,410 B2 | 11/2018 | Strobl et al. |
| 10,130,414 B2 | 11/2018 | Weiler et al. |
| 10,135,242 B2 | 11/2018 | Baber et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,194,911 B2 | 2/2019 | Miller et al. |
| 10,194,972 B2 | 2/2019 | Yates et al. |
| 10,194,976 B2 | 2/2019 | Boudreaux |
| 10,194,977 B2 | 2/2019 | Yang |
| 10,211,586 B2 | 2/2019 | Adams et al. |
| 10,231,776 B2 | 3/2019 | Artale et al. |
| 10,238,387 B2 | 3/2019 | Yates et al. |
| 10,245,095 B2 | 4/2019 | Boudreaux |
| 10,258,404 B2 | 4/2019 | Wang |
| 10,265,118 B2 | 4/2019 | Gerhardt |
| 10,278,721 B2 | 5/2019 | Dietz et al. |
| 10,307,203 B2 | 6/2019 | Wyatt |
| 10,314,638 B2 | 6/2019 | Gee et al. |
| 10,321,950 B2 | 6/2019 | Yates et al. |
| 10,342,602 B2 | 7/2019 | Strobl et al. |
| 10,413,352 B2 | 9/2019 | Thomas et al. |
| 10,420,607 B2 | 9/2019 | Woloszko et al. |
| 10,426,873 B2 | 10/2019 | Schultz |
| 10,433,900 B2 | 10/2019 | Harris et al. |
| 10,441,345 B2 | 10/2019 | Aldridge et al. |
| 10,463,421 B2 | 11/2019 | Boudreaux et al. |
| 10,478,243 B2 | 11/2019 | Couture et al. |
| 10,485,607 B2 | 11/2019 | Strobl et al. |
| 10,524,852 B1 | 1/2020 | Cagle et al. |
| 10,524,854 B2 | 1/2020 | Woodruff et al. |
| 10,575,868 B2 | 3/2020 | Hall et al. |
| 10,675,082 B2 | 6/2020 | Shelton, IV et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0049551 A1 | 4/2002 | Friedman et al. |
| 2002/0068931 A1* | 6/2002 | Wong .............. A61B 18/1206 606/34 |
| 2002/0077550 A1 | 6/2002 | Rabiner et al. |
| 2002/0095175 A1 | 7/2002 | Brock et al. |
| 2002/0107517 A1 | 8/2002 | Witt et al. |
| 2002/0133149 A1 | 9/2002 | Bessette |
| 2002/0156493 A1 | 10/2002 | Houser et al. |
| 2003/0014053 A1 | 1/2003 | Nguyen et al. |
| 2003/0055443 A1 | 3/2003 | Spotnitz |
| 2003/0066938 A1 | 4/2003 | Zimmerman |
| 2003/0109875 A1 | 6/2003 | Tetzlaff et al. |
| 2003/0114731 A1 | 6/2003 | Cadeddu et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0181910 A1 | 9/2003 | Dycus et al. |
| 2003/0204199 A1 | 10/2003 | Novak et al. |
| 2003/0212332 A1 | 11/2003 | Fenton et al. |
| 2003/0229344 A1 | 12/2003 | Dycus et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0073205 A1* | 4/2004 | Treat .................. A61B 18/1445 606/29 |
| 2004/0092921 A1 | 5/2004 | Kadziauskas et al. |
| 2004/0092992 A1 | 5/2004 | Adams et al. |
| 2004/0093039 A1 | 5/2004 | Schumert |
| 2004/0097919 A1 | 5/2004 | Wellman et al. |
| 2004/0097996 A1 | 5/2004 | Rabiner et al. |
| 2004/0102804 A1 | 5/2004 | Chin |
| 2004/0133089 A1 | 7/2004 | Kilcoyne et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0199193 A1 | 10/2004 | Hayashi et al. |
| 2004/0249367 A1 | 12/2004 | Saadat et al. |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2005/0015125 A1 | 1/2005 | Mioduski et al. |
| 2005/0033278 A1 | 2/2005 | McClurken et al. |
| 2005/0033337 A1 | 2/2005 | Muir et al. |
| 2005/0090817 A1 | 4/2005 | Phan |
| 2005/0096502 A1 | 5/2005 | Khalili |
| 2005/0119640 A1 | 6/2005 | Sverduk et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0192610 A1 | 9/2005 | Houser et al. |
| 2005/0215858 A1 | 9/2005 | Vail |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0272972 A1 | 12/2005 | Iddan |
| 2005/0273139 A1 | 12/2005 | Krauss et al. |
| 2005/0288555 A1 | 12/2005 | Binmoeller |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0159731 A1 | 7/2006 | Shoshan |
| 2006/0190034 A1 | 8/2006 | Nishizawa et al. |
| 2006/0211943 A1 | 9/2006 | Beaupre |
| 2006/0253050 A1 | 11/2006 | Yoshimine et al. |
| 2006/0270916 A1 | 11/2006 | Skwarek et al. |
| 2006/0293656 A1 | 12/2006 | Shadduck et al. |
| 2007/0008744 A1 | 1/2007 | Heo et al. |
| 2007/0010709 A1 | 1/2007 | Reinschke |
| 2007/0016235 A1 | 1/2007 | Tanaka et al. |
| 2007/0016236 A1 | 1/2007 | Beaupre |
| 2007/0020065 A1 | 1/2007 | Kirby |
| 2007/0032701 A1 | 2/2007 | Fowler et al. |
| 2007/0032704 A1 | 2/2007 | Gandini et al. |
| 2007/0032785 A1 | 2/2007 | Diederich et al. |
| 2007/0051766 A1 | 3/2007 | Spencer |
| 2007/0055228 A1 | 3/2007 | Berg et al. |
| 2007/0063618 A1 | 3/2007 | Bromfield |

(56) References Cited

U.S. PATENT DOCUMENTS

| | | |
|---|---|---|
| 2007/0073185 A1 | 3/2007 | Nakao |
| 2007/0073341 A1 | 3/2007 | Smith et al. |
| 2007/0106317 A1 | 5/2007 | Shelton et al. |
| 2007/0118115 A1 | 5/2007 | Artale et al. |
| 2007/0123748 A1 | 5/2007 | Meglan |
| 2007/0130771 A1 | 6/2007 | Ehlert et al. |
| 2007/0135686 A1 | 6/2007 | Pruitt et al. |
| 2007/0149881 A1 | 6/2007 | Rabin |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0182842 A1 | 8/2007 | Sonnenschein et al. |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0270651 A1 | 11/2007 | Gilad et al. |
| 2007/0275348 A1 | 11/2007 | Lemon |
| 2007/0276424 A1 | 11/2007 | Mikkaichi et al. |
| 2007/0287933 A1 | 12/2007 | Phan et al. |
| 2008/0015413 A1 | 1/2008 | Barlow et al. |
| 2008/0015575 A1 | 1/2008 | Odom et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0082039 A1 | 4/2008 | Babaev |
| 2008/0082098 A1 | 4/2008 | Tanaka et al. |
| 2008/0103495 A1* | 5/2008 | Mihori ............... A61B 18/1206 606/38 |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208231 A1 | 8/2008 | Ota et al. |
| 2008/0214967 A1 | 9/2008 | Aranyi et al. |
| 2008/0228179 A1* | 9/2008 | Eder ................ A61B 18/1442 606/33 |
| 2008/0234709 A1 | 9/2008 | Houser |
| 2008/0281200 A1 | 11/2008 | Voic et al. |
| 2008/0281315 A1 | 11/2008 | Gines |
| 2008/0287948 A1 | 11/2008 | Newton et al. |
| 2008/0300588 A1 | 12/2008 | Groth et al. |
| 2008/0312502 A1 | 12/2008 | Swain et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0143678 A1 | 6/2009 | Keast et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0248021 A1 | 10/2009 | McKenna |
| 2009/0254080 A1 | 10/2009 | Honda |
| 2009/0270771 A1 | 10/2009 | Takahashi |
| 2009/0270853 A1 | 10/2009 | Yachi et al. |
| 2009/0287205 A1 | 11/2009 | Ingle |
| 2010/0036370 A1 | 2/2010 | Mirel et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0158307 A1 | 6/2010 | Kubota et al. |
| 2010/0187283 A1 | 7/2010 | Crainich et al. |
| 2010/0204802 A1 | 8/2010 | Wilson et al. |
| 2010/0222752 A1 | 9/2010 | Collins, Jr. et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2011/0009857 A1 | 1/2011 | Subramaniam et al. |
| 2011/0028964 A1 | 2/2011 | Edwards |
| 2011/0087224 A1 | 4/2011 | Cadeddu et al. |
| 2011/0125151 A1* | 5/2011 | Strauss ............... A61B 18/1206 606/37 |
| 2011/0257680 A1 | 10/2011 | Reschke et al. |
| 2011/0270245 A1 | 11/2011 | Horner et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0041358 A1 | 2/2012 | Mann et al. |
| 2012/0078244 A1 | 3/2012 | Worrell et al. |
| 2012/0085358 A1 | 4/2012 | Cadeddu et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0194864 A1 | 7/2014 | Martin et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0263541 A1 | 9/2014 | Leimbach et al. |
| 2014/0263552 A1 | 9/2014 | Hall et al. |
| 2014/0350540 A1 | 11/2014 | Kitagawa et al. |
| 2015/0032170 A1 | 1/2015 | Ishida et al. |
| 2015/0080876 A1 | 3/2015 | Worrell et al. |
| 2015/0250531 A1 | 9/2015 | Dycus et al. |
| 2015/0257819 A1 | 9/2015 | Dycus et al. |
| 2015/0272571 A1 | 10/2015 | Leimbach et al. |
| 2015/0272659 A1 | 10/2015 | Boudreaux et al. |
| 2015/0327918 A1 | 11/2015 | Sobajima et al. |
| 2016/0045248 A1 | 2/2016 | Unger et al. |
| 2016/0051316 A1 | 2/2016 | Boudreaux |
| 2016/0066980 A1 | 3/2016 | Schall et al. |
| 2016/0100747 A1 | 4/2016 | Nitsan et al. |
| 2016/0143687 A1 | 5/2016 | Hart et al. |
| 2016/0157923 A1 | 6/2016 | Ding |
| 2016/0157927 A1 | 6/2016 | Corbett et al. |
| 2016/0175029 A1 | 6/2016 | Witt et al. |
| 2016/0199124 A1 | 7/2016 | Thomas et al. |
| 2016/0199125 A1 | 7/2016 | Jones |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296270 A1 | 10/2016 | Strobl et al. |
| 2017/0056097 A1 | 3/2017 | Monson et al. |
| 2017/0105787 A1 | 4/2017 | Witt et al. |
| 2017/0105789 A1 | 4/2017 | Boudreaux et al. |
| 2017/0135751 A1 | 5/2017 | Rothweiler et al. |
| 2017/0164972 A1 | 6/2017 | Johnson et al. |
| 2017/0189102 A1 | 7/2017 | Hibner et al. |

(56) References Cited

U.S. PATENT DOCUMENTS

| | | |
|---|---|---|
| 2017/0312014 A1 | 11/2017 | Strobl et al. |
| 2017/0312015 A1 | 11/2017 | Worrell et al. |
| 2017/0312017 A1 | 11/2017 | Trees et al. |
| 2017/0312018 A1 | 11/2017 | Trees et al. |
| 2017/0312019 A1 | 11/2017 | Trees et al. |
| 2017/0325878 A1 | 11/2017 | Messerly et al. |
| 2017/0325886 A1 | 11/2017 | Graham et al. |
| 2018/0085156 A1 | 3/2018 | Witt et al. |
| 2018/0125571 A1 | 5/2018 | Witt et al. |
| 2018/0228530 A1 | 8/2018 | Yates et al. |
| 2018/0263683 A1 | 9/2018 | Renner et al. |
| 2018/0280075 A1 | 10/2018 | Nott et al. |
| 2018/0368906 A1 | 12/2018 | Yates et al. |
| 2019/0000468 A1 | 1/2019 | Adams et al. |
| 2019/0000470 A1 | 1/2019 | Yates et al. |
| 2019/0000528 A1 | 1/2019 | Yates et al. |
| 2019/0000530 A1 | 1/2019 | Yates et al. |
| 2019/0000555 A1 | 1/2019 | Schings et al. |
| 2019/0059980 A1 | 2/2019 | Shelton, IV et al. |
| 2019/0099209 A1 | 4/2019 | Witt et al. |
| 2019/0099212 A1 | 4/2019 | Davison et al. |
| 2019/0099213 A1 | 4/2019 | Witt et al. |
| 2019/0099217 A1 | 4/2019 | Witt et al. |

FOREIGN PATENT DOCUMENTS

| | | |
|---|---|---|
| CN | 2868227 Y | 2/2007 |
| DE | 4300307 A1 | 7/1994 |
| DE | 29623113 U1 | 10/1997 |
| DE | 20004812 U1 | 9/2000 |
| DE | 10201569 A1 | 7/2003 |
| DE | 102005032371 A1 | 1/2007 |
| EP | 0171967 A2 | 2/1986 |
| EP | 0705571 A1 | 4/1996 |
| EP | 1862133 A1 | 12/2007 |
| EP | 2060238 A1 | 5/2009 |
| EP | 1747761 B1 | 10/2009 |
| EP | 1767164 B1 | 1/2013 |
| EP | 2578172 A2 | 4/2013 |
| ES | 2419159 A2 | 8/2013 |
| GB | 2032221 A | 4/1980 |
| JP | S537994 A | 1/1978 |
| JP | H08229050 A | 9/1996 |
| JP | 2002186627 A | 7/2002 |
| JP | 2009213878 A | 9/2009 |
| JP | 2010057926 A | 3/2010 |
| WO | WO-8103272 A1 | 11/1981 |
| WO | WO-9314708 A1 | 8/1993 |
| WO | WO-9800069 A1 | 1/1998 |
| WO | WO-9923960 A1 | 5/1999 |
| WO | WO-0024330 A1 | 5/2000 |
| WO | WO-0128444 A1 | 4/2001 |
| WO | WO-02080794 A1 | 10/2002 |
| WO | WO-2004078051 A2 | 9/2004 |
| WO | WO-2008130793 A1 | 10/2008 |
| WO | WO-2009067649 A2 | 5/2009 |
| WO | WO-2010104755 A1 | 9/2010 |
| WO | WO-2011008672 A2 | 1/2011 |
| WO | WO-2011044343 A2 | 4/2011 |
| WO | WO-2011144911 A1 | 11/2011 |
| WO | WO-2012044606 A2 | 4/2012 |
| WO | WO-2012061638 A1 | 5/2012 |
| WO | WO-2013131823 A1 | 9/2013 |

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=Ml&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

National Semiconductors Temperature Sensor Handbook—http://www.national.com/appinfo/tempsensors/files/temphb.pdf; accessed online: Apr. 1, 2011.

Chen et al., "Heat-induced changes in the mechanics of a collagenous tissue: pseudoelastic behavior at 37° C.," Journal of Biomechanics, 31, pp. 211-216 (1998).

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Kurt Gieck & Reiner Gieck, *Engineering Formulas* § Z.7 (7th ed. 1997).

Leonard I. Malis, M.D., "The Value of Irrigation During Bipolar Coagulation," 1989.

Covidien Brochure, The LigaSure Precise™ Instrument, dated Mar. 2011 (2 pages).

Covidien Brochure, [Value Analysis Brief], LigaSure Advance™ Pistol Grip, dated Rev. Apr. 2010 (7 pages).

Covidien Brochure, LigaSure Impact™ Instrument LF4318, dated Feb. 2013 (3 pages).

Covidien Brochure, LigaSure Atlas™ Hand Switching Instruments, dated Dec. 2008 (2 pages).

Covidien Brochure, The LigaSure™ 5 mm Blunt Tip Sealer/Divider Family, dated Apr. 2013 (2 pages).

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Sullivan, "Optimal Choice for Number of Strands in a Litz-Wire Transformer Winding," IEEE Transactions on Power Electronics, vol. 14, No. 2, Mar. 1999, pp. 283-291.

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

Glaser and Subak-Sharpe, Integrated Circuit Engineering, Addison-Wesley Publishing, Reading, MA (1979). (book—not attached).

Abbott, et al. Proceedings of the 2007 IEEEIRDJ International Conference on Intelligent Robots and Systems. 410-416, 2007.

(56) References Cited

OTHER PUBLICATIONS

Cadeddu et al., "Magnetic positioning system for trocarless laparoscopic instruments," American College of Surgeons Poster, 2004.
Cadeddu et al., "Novel magnetically guided intra-abdominal camera to facilitate laparoendoscopic single site surgery: initial human experience," Surgical Endoscopy, SAGES Oral Manuscript, 2009.
Cadeddu et al., "Transabdominal magnetic anchoring system for trocar-less laparoscopic surgery," American Urological Association Poster, 2002.
Cadeddu et al., "Transabdominal magnetic anchoring system for trocar-less laparoscopic surgery," Journal of Urology Abstract, 2002.
Castellvi et al., "Completely transvaginal NOTES cholecystectomy in a porcine model using novel endoscopic instrumentation," Accepted for Poster Presentation, SAGES Annual Meeting, 2009.
Castellvi et al., "Hybrid transgastric NOTES cholecystectomy in a porcine model using a magnetically anchored cautery and novel instrumentation," Submitted for Presentation, ASGE, 2009.
Castellvi et al., "Hybrid transvaginal NOTES sleeve gastrectomy in a porcine model using a magnetically anchored camera and novel instrumentation," Accepted for Poster Presentation, SAGES Annual Meeting, 2009.
Duchene et al., "Magnetic positioning system for trocarless laparoscopic instruments," Engineering and Urology Society Poster, 2004.
Fernandez et al., "Development of a transabdominal anchoring system for trocar-less laparoscopic surgery," ASME Proceedings of/MECE, 2003.
Gedeon et al., "Maximizing coupling strength of magnetically anchored notes instruments: How thick can we go?" Submittedfor Presentation, Poster, SAGES Annual Meeting, 2008.
Gedeon et al., "Maximizing coupling strength of magnetically anchored notes instruments: How thick can we go?" SAGES Annual Meeting Poster, 2008.
Park et al., "Trocar-less Instrumentation for Laparoscopy: Magnetic Positioning of Intra-Abdominal Camera and Retractor", Annals of Surgery, vol. 245, No. 3, pp. 379-384, Mar. 2007.
Peirs et al., "A miniature manipulator for integration in self-propelling endoscope," Sensors and Actuators, 92:343-9, 2001.
Raman et al., "Complete transvaginal NOTES nephrectomy using magnetically anchored instrumentation," Journal of Endourology, 23(3):, 2009.367-371,2009.
Rapaccini et al., "Gastric Wall Thickness in Normal and Neoplastic Subjects: A Prospective Study Performed by Abdominal Ultrasound", Gastrointestinal Radiology, vol. 13, pp. 197-199. 1988.
Scott et al., "A randomized comparison of laparoscopic, flexible endoscopic, and wired and wireless magnetic NOTES cameras on ex-vivo and in-vivo surgical performance," Digestive Disease Week (DDW), American Society for Gastrointestinal Endoscopy (ASGE) Annual Meeting Abstract, 2008.
Scott et al., "Completely transvaginal NOTES cholecystectomy using magnetically anchored instruments," Surg. Endosc., 21:2308-2316, 2007.
Scott et al., "Evaluation of a novel air seal access port for transvaginal notes cholecystectomy," Submitted for Presentation, SAGES Annual Meeting, 2008.
Scott et al., "Magnetically anchored instruments for transgastric endoscopic surgery," Oral Presentation for SAGES Annual Meeting, Emerging Technology Oral Abstract ET005, 2006.
Scott et al., "Optimizing magnetically anchored camera, light source, graspers, and cautery dissector for transvaginal notes cholecystectomy," Submitted for Presentation, SAGES Annual Meeting, 2008.
Scott et al., "Short-term survival outcomes following transvaginal NOTES cholecystectomy using magnetically anchored instruments," Oral Presentation, ASGE Annual Meeting/DDW, 2007.
Scott et al., "Trans gastric, transcolonic, and transvaginal cholecystectomy using magnetically anchored instruments," SAGES Annual Meeting Poster, 2007.
Scott et al., "Transvaginal NOTES cholecystectomy using magnetically anchored instruments," Abstract for Video Submission, ASGE II1h Annual Video Forum, 2007.
Scott et al., "Transvaginal single access 'pure' NOTES sleeve gastrectomy using a deployable magnetically anchored video camera," Digestive Disease Week (DDW), American Society for Gastrointestinal Endoscopy (ASGE) Annual Meeting Poster, 2008.
Swain et al., "Linear stapler formation of ileo-rectal, entero-enteral and gastrojejunal anastomoses during dual and single access 'pure' NOTES procedures: Methods, magnets and stapler modifications," Digestive Disease Week (DDW), American Society for Gastrointestinal Endoscopy (ASGE) Annual Meeting Abstract, 2008.
Swain et al., "Wireless endosurgery for NOTES," Digestive Disease Week (DDW), American Society for Gastrointestinal Endoscopy (ASGE) Annual Meeting Abstract, 2008.
Tang et al., "Live video manipulator for endoscopy and natural orifice transluminal endoscopic surgery (with videos)," Gastrointestinal Endoscopy, 68:559-564, 2008.
Zeltser et al., "Single trocar laparoscopic nephrectomy using magnetic anchoring and guidance system in the porcine model," The Journal of Urology, 178:288-291, 2007.
Wright, et al., "Time-Temperature Equivalence of Heat-Induced Changes in Cells and Proteins," Feb. 1998. ASME Journal of Biomechanical Engineering, vol. 120, pp. 22-26.
Douglas, S.C. "Introduction to Adaptive Filter". Digital Signal Processing Handbook. Ed. Vijay K. Madisetti and Douglas B. Williams. Boca Raton: CRC Press LLC, 1999.
Jang, J. et al. "Neuro-fuzzy and Soft Computing." Prentice Hall, 1997, pp. 13-89, 199-293, 335-393, 453-496, 535-549.
Erbe Electrosurgery VIO® 200 S, (2012), p. 7, 12 pages, accessed Mar. 31, 2014 at http://www.erbe-med.com/erbe/media/Marketing materialien/85140170 ERBE EN VIO 200 S D027541.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
F. A. Duck, "Optical Properties of Tissue Including Ultraviolet and Infrared Radiation," pp. 43-71 in Physical Properties of Tissue (1990).
Orr et al., "Overview of Bioheat Transfer," pp. 367-384 in Optical-Thermal Response of Laser-Irradiated Tissue, A. J. Welch and M. J. C. van Gernert, eds., Plenum, New York (1995).
Campbell et al, "Thermal Imaging in Surgery," p. 19-3, in Medical Infrared Imaging, N. A. Diakides and J. D. Bronzino, Eds. (2008).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Technology Overview, printed from www.harmonicscalpel.com, Internet site, website accessed on Jun. 13, 2007, (3 pages).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Hörmann et al., "Reversible and irreversible denaturation of collagen fibers." Biochemistry, 10, pp. 932-937 (1971).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.

\* cited by examiner

PRIOR ART

MEDICAL DEVICE

This application is a divisional application filed under 35 U.S.C § 121 of U.S. patent application Ser. No. 13/810,865, titled MEDICAL DEVICE, filed Sep. 11, 2013, now U.S. Pat. No. 9,707,027, which is a U.S. national phase application filed under 35 U.S.C. § 371 of International Patent Application No. PCT/GB2011/000778, titled MEDICAL DEVICE, filed May 20, 2011, which application claims priority to Great Britain Patent Application No. 1008510.8 filed May 21, 2010, the disclosures of which are herein incorporated by reference.

The present invention relates to the field of medical devices and in particular, although not exclusively, to medical cauterization and cutting devices. The invention also relates to drive circuits and methods for driving such medical devices.

Many surgical procedures require cutting or ligating blood vessels or other internal tissue. Many surgical procedures are performed using minimally invasive techniques, a hand-held cauterization device is used by the surgeon to perform the cutting or ligating. The existing hand-held cauterization devices require a desk top power supply and control electronics that are connected to the device through an electrical supply line. FIG. 10 illustrates such an existing hand-held cauterization device currently in use.

It has been known for a number of years that these existing devices are cumbersome and difficult to use during a surgical operation due to the large size of the supply and control electronics and due to the tethering of the hand-held cauterization device to the supply and control electronics. It has also been known for a number of years that these problems would be overcome by providing a battery powered hand-held cauterization device in which the power and control electronics are mounted within the device itself, such as within the handle of the device. However, it is not a simple matter of miniaturising the electronics. The power that has to be supplied to the device during the surgical procedure and the current design of the electronics is such that large capacitors, inductors and transformers as well as heat sinks and fans are required. FIG. 11 illustrates in more detail the different parts of the supply and control electronics that are used in the existing design as illustrated in FIG. 10. Whilst it is possible to reduce the size of the sensing and control electronics, other parts of the circuitry cannot be miniaturised in this way.

In particular, the existing electronics design uses circuitry for providing an adjustable 24 Volt power supply; FETs and associated drive circuitry; a transformer for increasing the supply voltage; and filtering circuitry to remove harmonics from the square wave voltage levels that are generated by the FET switches and the transformer. Given the voltage levels and the power levels used to drive the cauterization device, the transformers and output filters all have to be relatively bulky devices and large heat sinks and a fan are required to cool the FET switches.

The present invention aims to provide an alternative circuit design that will allow the miniaturisation of the circuitry so that it can be built into the hand-held cauterization device, whilst still being able to provide the power and control required for the medical procedure.

The present invention provides a medical device comprising an end effector having at least one electrical contact a radio frequency, RF, generation circuit for generating an RF drive signal and to provide the RF drive signal to the at least one electrical contact and wherein the RF generation circuit comprises a resonant circuit. In one embodiment, the radio frequency generation circuit comprises switching circuitry that generates a cyclically varying signal, such as a square wave signal, from a DC supply and the resonant circuit is configured to receive the cyclically varying signal from the switching circuitry. The DC supply is preferably provided by one or more batteries that can be mounted in a housing (such as a handle) of the device.

According to another aspect, the invention provides a medical device comprising: a handle for gripping by a user; an end effector coupled to the handle, the end effector having at least one electrical contact; battery terminals for connecting to one or more batteries; a radio frequency, RF, generation circuit coupled to said battery terminals and operable to generate an RF drive signal and to provide the RF drive signal to the at least one electrical contact of said end effector; wherein the frequency generation circuit comprises: switching circuitry for generating a cyclically varying signal (which may be a square wave pulse width modulated signal) from a potential difference across said battery terminals; and a resonant drive circuit coupled to said switching circuitry and operable to filter the cyclically varying signal generated by the switching circuitry; and wherein the RF drive signal is obtained using an output signal from said resonant circuit.

The medical device may also comprise a control circuit (which may comprise hardware and/or software) that varies the frequency of the RF drive signal. The control circuit may vary the frequency based on a measurement of the RF drive signal in order to control at least one of the power, voltage and/or current delivered to the at least one electrical contact of the end effector. In a preferred embodiment, the measurement is obtained from a sampling circuit that operates synchronously with respect to the frequency of the RF drive signal. The frequency at which the sampling circuit samples the sensed signal may be an integer fraction of the frequency of the RF drive signal.

In one embodiment, the control circuit varies the frequency of the RF drive signal around (preferably just above or just below) the resonant frequency of the resonant circuit. The resonant characteristic of the resonant circuit may vary with a load connected to the at least one electrical contact and the control circuit may be arranged to vary the RF drive frequency to track changes in the resonant characteristic of the resonant circuit.

According to another aspect, the invention provides a medical device comprising: a handle for gripping by a user; an end effector coupled to the handle and having at least one electrical contact; a radio frequency, RF, generation circuit operable to generate an RF drive signal and to provide the RF drive signal to the at least one electrical contact; and a control circuit operable to vary the frequency of the RF drive signal to control at least one of the power, the voltage and the current provided to the at least one contact of the end effector.

The RF generation circuit may comprise a signal generator that generates a cyclically varying signal at the RF frequency; and a frequency dependent attenuator that attenuates the cyclically varying signal in dependence upon the frequency of the cyclically varying signal. The frequency dependent attenuator may be a lossless attenuator and may comprise a resonant circuit having a resonant frequency at or near the RF frequency of the cyclically varying signal.

The present invention also provides a medical device comprising: a handle for gripping by a user; an end effector coupled to the handle and having at least one electrical contact; a radio frequency, RF, generation circuit operable to generate an RF drive signal and to provide the RF drive signal to the at least one electrical contact; an input for receiving a sensed signal that varies with the RF drive signal applied to the at least one electrical contact; a sampling circuit for sampling the sensed signal received at said input; a measurement circuit operable to make measurements of the RF drive signal using samples obtained from the sampling circuit; and a control circuit operable to control the RF generation circuit in dependence upon the measurements made by the measurement circuit, to vary the frequency of the generated RF drive signal; wherein the sampling circuit is operable to sample the sensed signal at a sampling frequency that varies in synchronism with the frequency of the RF drive signal.

The invention also provides a method of operating a medical device comprising generating an RF signal and applying the RF signal to at least one electrode of an end effector of the medical device and controlling the frequency of the generated RF signal to control at least one of the power, current, and voltage applied to the at least one electrode.

According to another aspect, the invention provides a method of cauterising a vessel or tissue, the method comprising: gripping the vessel or tissue with an end effector of a medical device; applying an RF signal to at least one electrode of the end effector that is in contact with the vessel or tissue; and controlling the frequency of the RF signal to control at least one of the power, current, and voltage applied to the tissue to perform the cauterisation.

The above methods may use the above described medical device, although that is not essential.

The controlling step may vary the frequency of the RF signal to control the power applied to the tissue or vessel, and the method may further comprise obtaining measurements of the impedance of the tissue or vessel and varying the desired power applied to the tissue or vessel in dependence upon the obtained impedance measurements.

These and various other features and aspects of the invention will become apparent from the following detailed description of embodiments which are described with reference to the accompanying Figures in which:

FIG. 5b illustrates a resulting power plot obtained by combining the current and voltage plots illustrated in FIG. 5a;

MEDICAL DEVICE

Many surgical procedures require cutting or ligating blood vessels or other vascular tissue. With minimally invasive surgery, surgeons perform surgical operations through a small incision in the patient's body. As a result of the limited space, surgeons often have difficulty controlling bleeding by clamping and/or tying-off transected blood vessels. By utilizing electrosurgical forceps, a surgeon can cauterize, coagulate/desiccate, and/or simply reduce or slow bleeding by controlling the electrosurgical energy applied through jaw members of the electrosurgical forceps.

Figure 1:
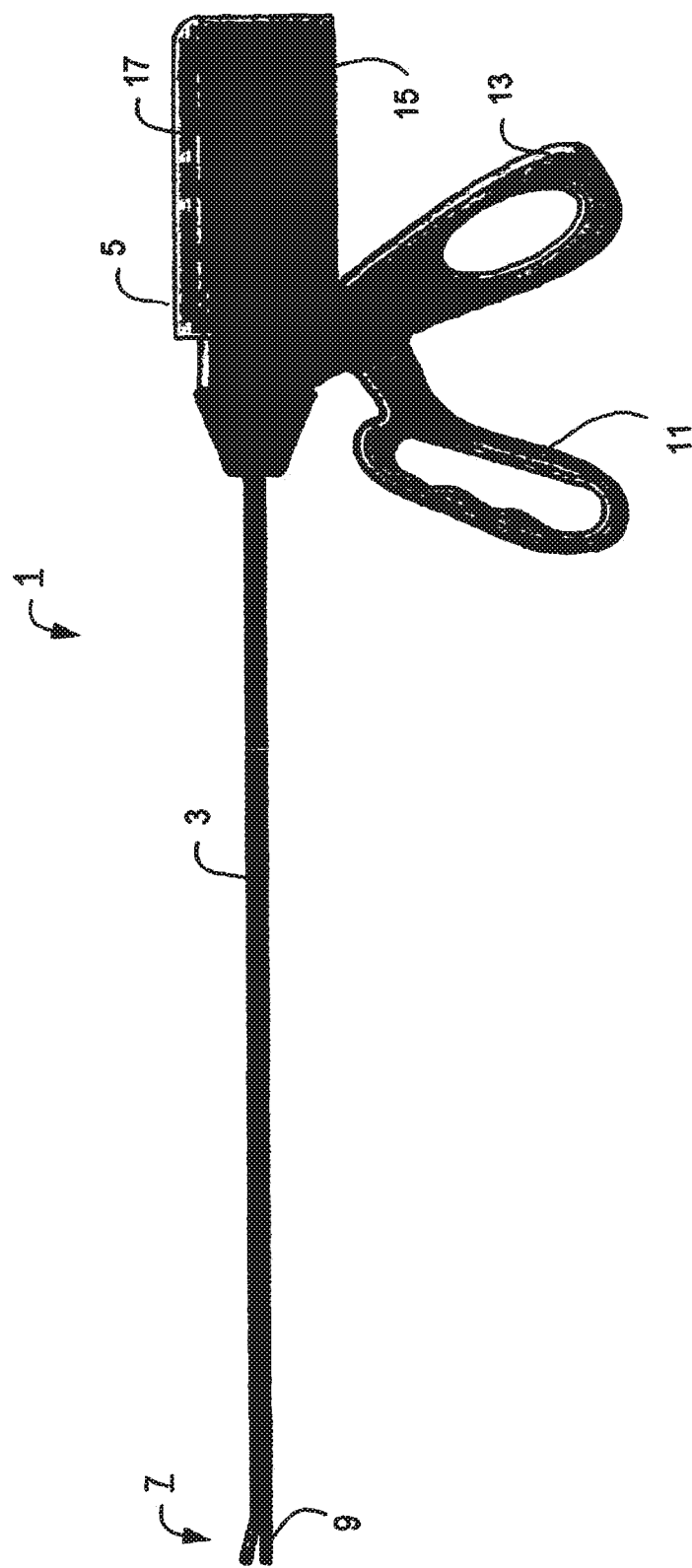
FIG. 1 illustrates a hand-held cauterization device that has batteries and drive and control circuitry mounted into a handle portion of the device.

FIG. 1 illustrates the form of an electrosurgical medical device 1 that is designed for minimally invasive medical procedures, according to one embodiment of the present invention. As shown, the device 1 is a self contained device, having an elongate shaft 3 that has a handle 5 connected to the proximal end of the shaft 3 and an end effector 7 connected to the distal end of the shaft 3. In this embodiment, the end effector 7 comprises medical forceps 9 and a cutting blade (not shown) that are controlled by the user manipulating control levers 11 and 13 of the handle 5.

During a surgical procedure, the shaft 3 is inserted through a trocar to gain access to the patient's interior and the operating site. The surgeon will manipulate the forceps 9 using the handle 5 and the control levers 11 and 13 until the forceps 9 are located around the vessel to be cauterised. Electrical energy at an RF frequency (it has been found that frequencies above about 50 kHz do not affect the human nervous system) is then applied, in a controlled manner, to the forceps 9 to perform the desired cauterisation. As shown in FIG. 1, in this embodiment, the handle 5 houses batteries 15 and control electronics 17 for generating and controlling the electrical energy required to perform the cauterisation. In this way, the device 1 is self contained in the sense that it does not need a separate control box and supply wire to provide the electrical energy to the forceps 9.

RF Drive Circuitry

Figure 2:
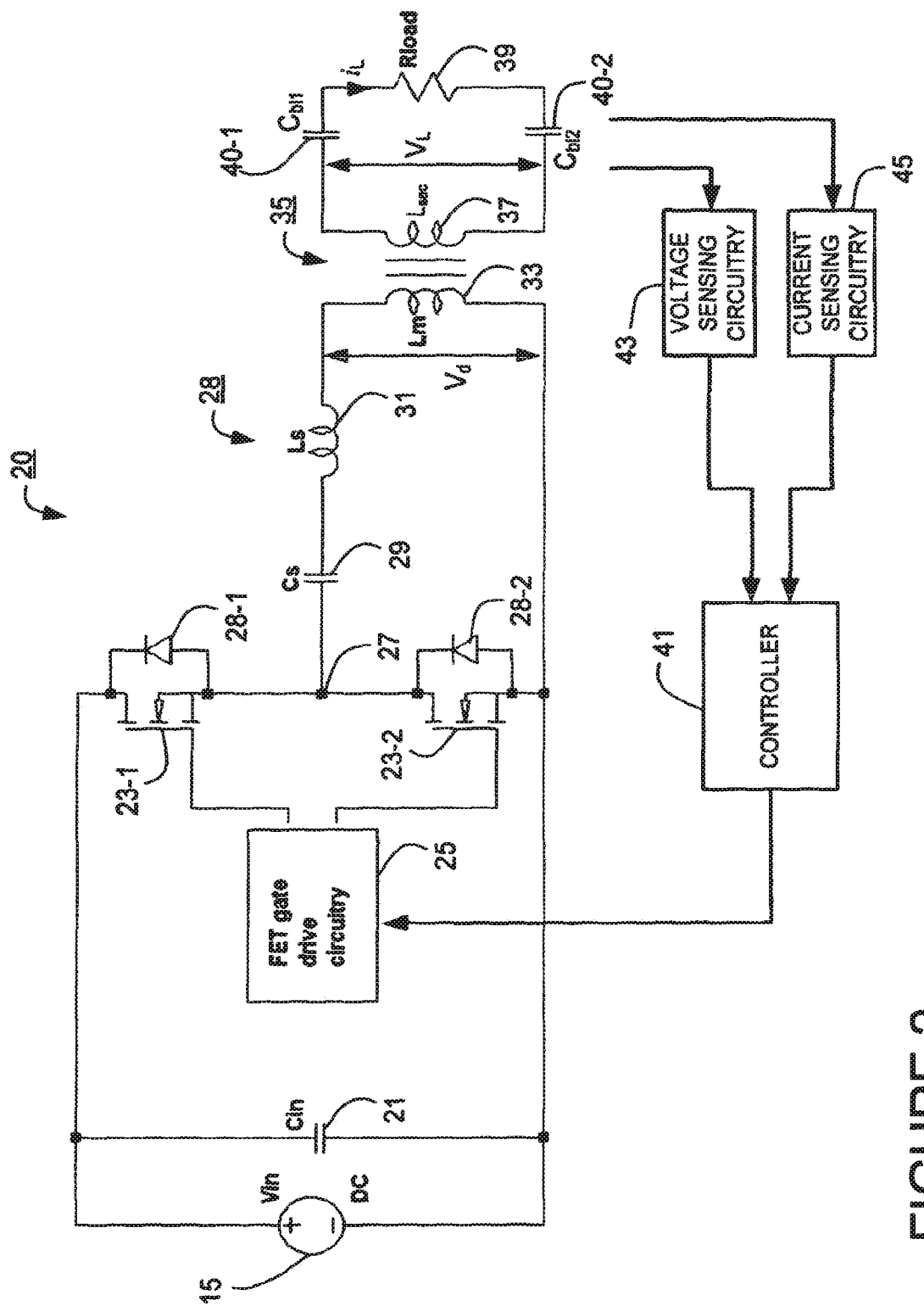
FIG. 2 is a part block part schematic diagram illustrating the main components of the RF drive circuitry and control circuitry used in one embodiment of the invention.

FIG. 2 is a part schematic part block diagram illustrating the RF drive and control circuitry 20 used in this embodiment to generate and control the RF electrical energy supplied to the forceps 9. As will be explained in more detail below, in this embodiment, the drive circuitry 20 is a resonant based circuit and the control circuitry operates to control the operating frequency of the drive signal so that it is varied around the resonant frequency of the drive circuit, which in turn controls the amount of power supplied to the forceps 9. The way that this is achieved will become apparent from the following description.

As shown in FIG. 2, the drive circuitry 20 comprises the above described batteries 15 that are arranged to supply, in this example, 0V and 24V rails. An input capacitor ($C_{in}$) 21 is connected between the 0V and the 24V rails for providing a low source impedance. A pair of FET switches 23-1 and 23-2 (both of which are N-channel in this embodiment to reduce power losses) is connected in series between the 0V rail and the 24V rail. FET gate drive circuitry 25 is provided that generates two drive signals—one for driving each of the two FETs 23. The FET gate drive circuitry 25 generates drive signals that causes the upper FET (23-1) to be on when the lower FET (23-2) is off and vice versa. This causes the node 27 to be alternately connected to the 24V rail (when FET 23-1 is switched on) and the 0V rail (when the FET 23-2 is switched on). FIG. 2 also shows the internal parasitic diodes 28-1 and 28-2 of the corresponding FETs 23, which conduct during any periods that the FETs 23 are open.

As shown in FIG. 2, the node 27 is connected to a capacitor-inductor-inductor resonant circuit 28 formed by capacitor $C_s$ 29, inductor $L_s$ 31 and inductor $L_m$ 33. The FET gate driving circuitry 25 is arranged to generate drive signals at a drive frequency ($f_d$) that opens and closes the FET switches 23 at around the resonant frequency of the resonant circuit 28. As a result of the resonant characteristic of the resonant circuit 28, the square wave voltage at node 27 will cause a substantially sinusoidal current at the drive frequency ($f_d$) to flow within the resonant circuit 28. As illustrated in FIG. 2, the inductor $L_m$ 33 is the primary of a transformer 35, the secondary of which is formed by inductor $L_{sec}$ 37. The transformer 35 up-converts the drive voltage ($V_d$) across inductor $L_m$ 33 to the load voltage ($V_L$) that is applied to the load (represented by the load resistance $R_{load}$ 39 in FIG. 2) corresponding to the impedance of the forceps' jaws and any tissue or vessel gripped by the forceps 9. As shown in FIG. 2, a pair of DC blocking capacitors $C_{bl}$ 40-1 and 40-2 is provided to prevent any DC signal being applied to the load 39.

In this embodiment, the amount of electrical power supplied to the forceps 9 is controlled by varying the frequency of the switching signals used to switch the FETs 23. This works because the resonant circuit 28 acts as a frequency dependent (lossless) attenuator. The closer the drive signal is to the resonant frequency of the resonant circuit 28, the less the drive signal is attenuated. Similarly, as the frequency of the drive signal is moved away from the resonant frequency of the circuit 28, the more the drive signal is attenuated and so the power supplied to the load reduces. In this embodiment, the frequency of the switching signals generated by the FET gate drive circuitry 25 is controlled by a controller 41 based on a desired power to be delivered to the load 39 and measurements of the load voltage ($V_L$) and of the load current ($i_L$) obtained by conventional voltage sensing circuitry 43 and current sensing circuitry 45. The way that the controller 41 operates will be described in more detail below.

Controller

Figure 3:
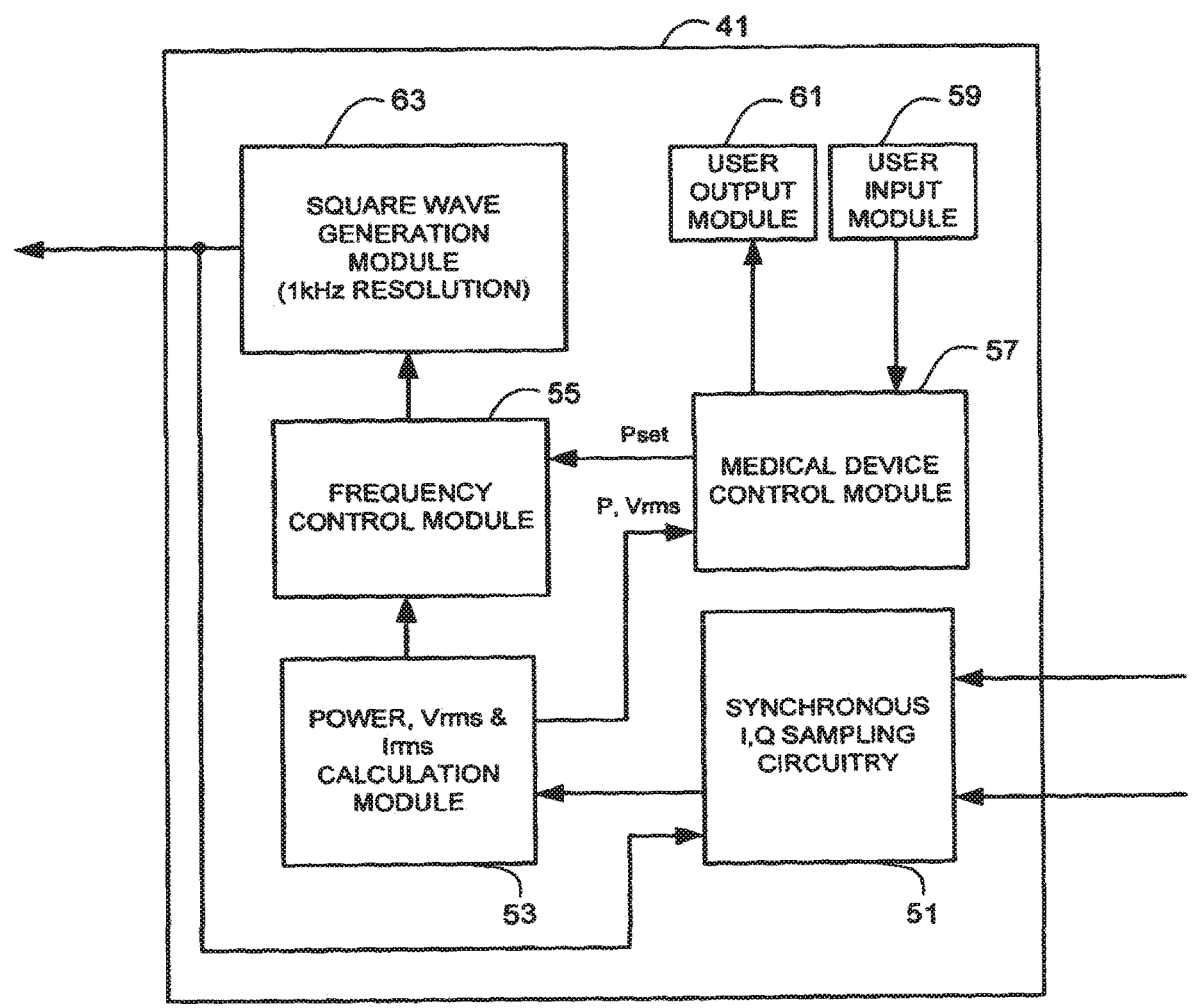
FIG. 3 is a block diagram illustrating the main components of a controller used to control the operation of the RF drive circuitry illustrated in FIG. 2.

FIG. 3 is a block diagram illustrating the main components of the controller 41. In this embodiment, the controller 41 is a micro-processor based controller and so most of the components illustrated in FIG. 3 are software based components. However, a hardware based controller 41 may be used instead. As shown, the controller 41 includes synchronous I,Q sampling circuitry 51 that receives the sensed voltage and current signals from the sensing circuitry 43 and 45 and obtains corresponding samples which are passed to a power, $V_{rms}$ and $I_{rms}$ calculation module 53. The calculation module 53 uses the received samples to calculate the RMS voltage and RMS current applied to the load 39 (forceps 9 and tissue/vessel gripped thereby) and from them the power that is presently being supplied to the load 39. The determined values are then passed to a frequency control module 55 and a medical device control module 57. The medical device control module 57 uses the values to determine the present impedance of the load 39 and based on this determined impedance and a pre-defined algorithm, determines what set point power ($P_{set}$) should be applied to the frequency control module 55. The medical device control module 57 is in turn controlled by signals received from a user input module 59 that receives inputs from the user (for example pressing buttons or activating the control levers 11 or 13 on the handle 5) and also controls output devices (lights, a display, speaker or the like) on the handle 5 via a user output module 61.

The frequency control module 55 uses the values obtained from the calculation module 53 and the power set point ($P_{set}$) obtained from the medical device control module 57 and predefined system limits (to be explained below), to determine whether or not to increase or decrease the applied frequency. The result of this decision is then passed to a square wave generation module 63 which, in this embodiment, increments or decrements the frequency of a square wave signal that it generates by 1 kHz, depending on the received decision. As those skilled in the art will appreciate, in an alternative embodiment, the frequency control module 55 may determine not only whether to increase or decrease the frequency, but also the amount of frequency change required. In this case, the square wave generation module 63 would generate the corresponding square wave signal with the desired frequency shift. In this embodiment, the square wave signal generated by the square wave generation module 63 is output to the FET gate drive circuitry 25, which amplifies the signal and then applies it to the FET 23-1. The FET gate drive circuitry 25 also inverts the signal applied to the FET 23-1 and applies the inverted signal to the FET 23-2.

Drive Signals and Signal Measurements

Figure 4:
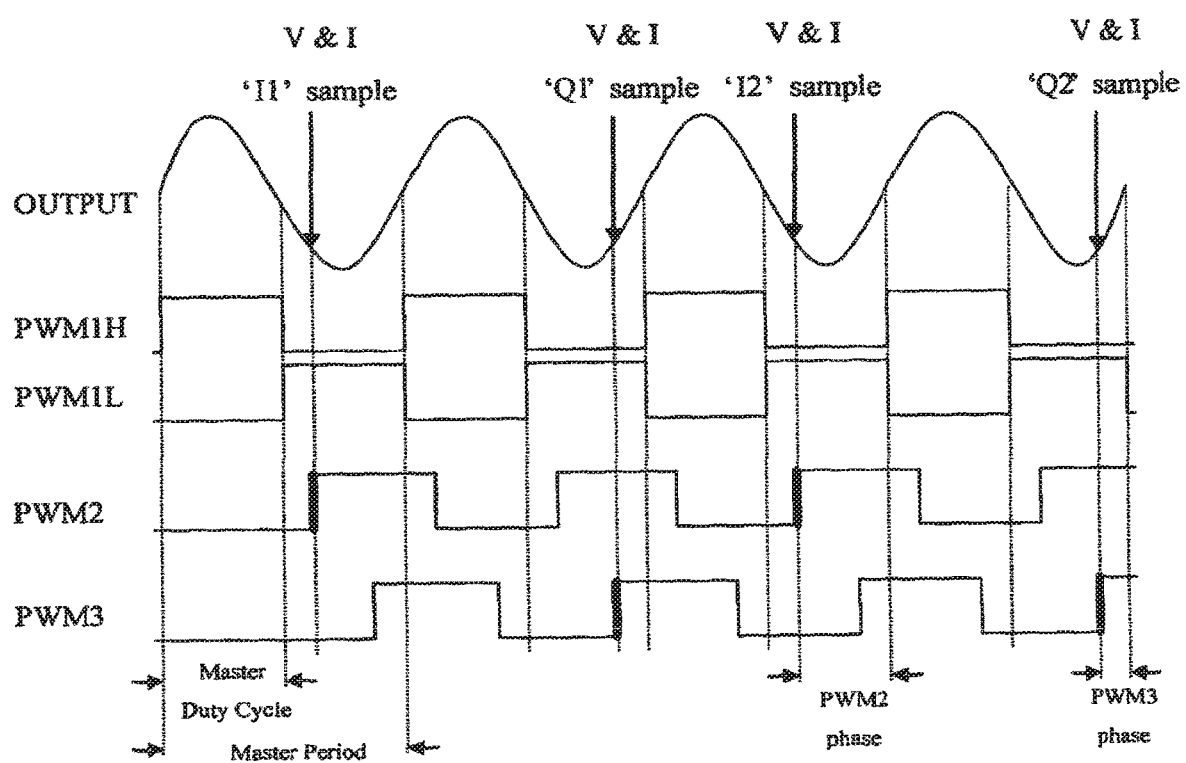
FIG. 4 is a timing diagram illustrating the RF drive signals applied to the cauterization device and illustrating a way in which synchronous samples may be obtained to measure the drive signals.

FIG. 4 is a signal plot illustrating the switching signals applied to the FETs 23; a sinusoidal signal representing the measured current or voltage applied to the load 39; and the timings when the synchronous sampling circuitry 51 samples the sensed load voltage and load current. In particular, FIG. 4 shows the switching signal (labelled PWM1H) applied to upper FET 23-1 and the switching signal (labelled PWM1L) applied to lower FET 23-2. Although not illustrated for simplicity, there is a dead time between PWM1H and PWM1L to ensure that that both FETs 23 are not on at the same time. FIG. 4 also shows the measured load voltage/current (labelled OUTPUT). Both the load voltage and the load current will be a sinusoidal waveform, although they may be out of phase, depending on the impedance of the load 39. As shown, the load current and load voltage are at the same drive frequency ($f_d$) as the switching signals (PWM1H and PWM1L) used to switch the FETs 23. Normally, when sampling a sinusoidal signal, it is necessary to sample the signal at a rate corresponding to at least twice the frequency of the signal being sampled—i.e. two samples per period. However, as the controller 41 knows the frequency of the switching signals, the synchronous sampling circuit 51 can sample the measured voltage/current signal at a lower rate. In this embodiment, the synchronous sampling circuit 51 samples the measured signal once per period, but at different phases in adjacent periods. In FIG. 4, this is illustrated by the "I" sample and the "Q" sample. The timing that the synchronous sampling circuit 51 makes these samples is controlled, in this embodiment, by the two control signals PWM2 and PWM3, which have a fixed phase relative to the switching signals (PWM1H and PWM1L) and are out of phase with each other (preferably by quarter of the period as this makes the subsequent calculations easier). As shown, the synchronous sampling circuit 51 obtains an "I" sample on every other rising edge of the PWM2 signal and the synchronous sampling circuit 51 obtains a "Q" sample on every other rising edge of the PWM3 signal. The synchronous sampling circuit 51 generates the PWM2 and PWM3 control signals from the square wave signal output by the square wave generator 63 (which is at the same frequency as the switching signals PWM1H and PWM1L). Thus when the frequency of the switching signals is changed, the frequency of the sampling control signals PWM2 and PWM3 also changes (whilst their relative phases stay the same). In this way, the sampling circuitry 51 continuously changes the timing at which it samples the sensed voltage and current signals as the frequency of the drive signal is changed so that the samples are always taken at the same time points within the period of the drive signal. Therefore, the sampling circuit 51 is performing a "synchronous" sampling operation instead of a more conventional sampling operation that just samples the input signal at a fixed sampling rate defined by a fixed sampling clock.

The samples obtained by the synchronous sampling circuitry 51 are then passed to the power, $V_{rms}$ and $I_{rms}$ calculation module 53 which can determine the magnitude and phase of the measured signal from just one "I" sample and one "Q" sample of the load current and load voltage. However, in this embodiment, to achieve some averaging, the calculation module 53 averages consecutive "I" samples to provide an average "I" value and consecutive "Q" samples to provide an average "Q" value; and then uses the average I and Q values to determine the magnitude and phase of the measured signal (in a conventional manner). As those skilled in the art will appreciate, with a drive frequency of about 400 kHz and sampling once per period means that the synchronous sampling circuit 51 will have a sampling rate of 400 kHz and the calculation module 53 will produce a voltage measure and a current measure every 0.01 ms. The operation of the synchronous sampling circuit 51 offers an improvement over existing products, where measurements can not be made at the same rate and where only magnitude information is available (the phase information being lost).

Limits

As with any system, there are certain limits that can be placed on the power, current and voltage that can be delivered to the forceps 9. The limits used in this embodiment and how they are controlled will now be described.

Figure 5A:
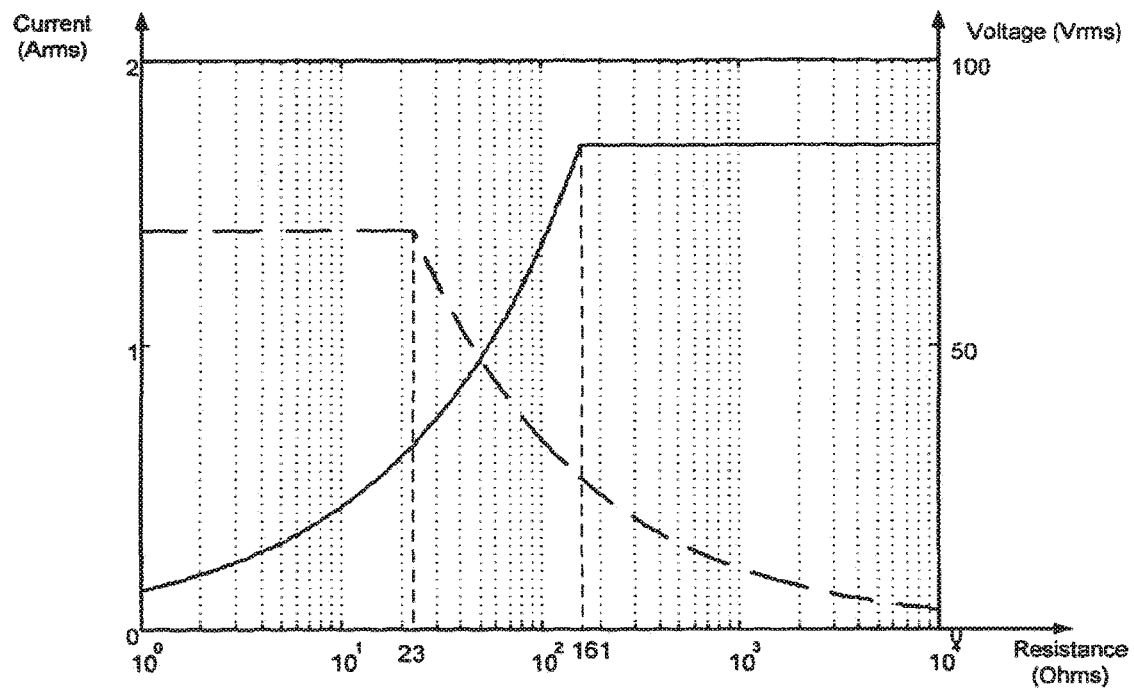
FIG. 5a is a plot illustrating limits that are placed on voltage and current supplied to the cauterization device illustrated in FIG. 1.
Figure 5B:
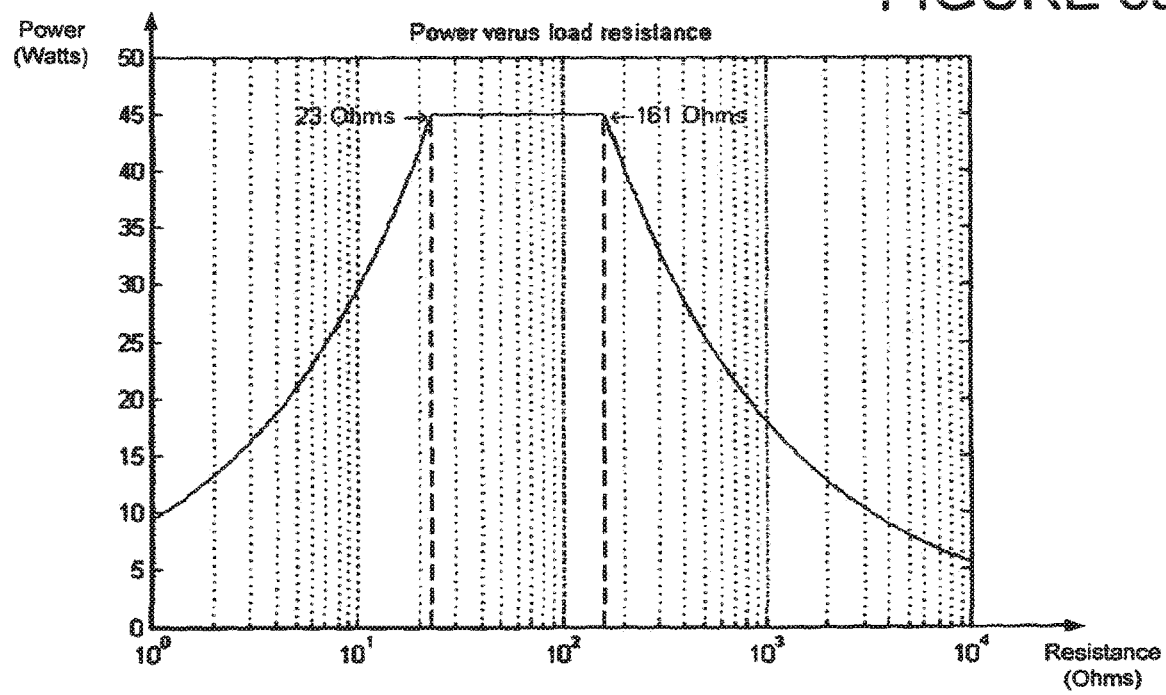

In this embodiment, the RF drive circuitry 20 is designed to deliver a power limited sine wave into tissue with the following requirements:
1) Supplied with a nominally 24V DC supply
2) Substantially sinusoidal output waveform at approximately 400 kHz
3) Power limited output of 45 W
4) Current limited to 1.4 $A_{rms}$ and voltage limited to 85$V_{rms}$ The last two requirements are represented graphically in FIGS. 5a and 5b. In particular, FIG. 5a illustrates idealised plots of voltage and current for loads between 1 Ohm and 10 k Ohms on a logarithmic scale; and FIG. 5b illustrates the power delivered to the load 39 for loads between 1 Ohm and 10 k Ohms.

The frequency control module 55 maintains data defining these limits and uses them to control the decision about whether to increase or decrease the excitation frequency.

Resonant Characteristic and Frequency Control

As mentioned above, the amount of electrical power supplied to the forceps 9 is controlled by varying the frequency of the switching signals used to switch the FETs 23. This is achieved by utilising the fact that the impedance of the resonant circuit 28 changes rapidly with frequency. Therefore by changing the frequency of the switching signals, the magnitude of the current through the resonant circuit 28, and hence through the load 39, can be varied as required to regulate the output power.

Figure 6:
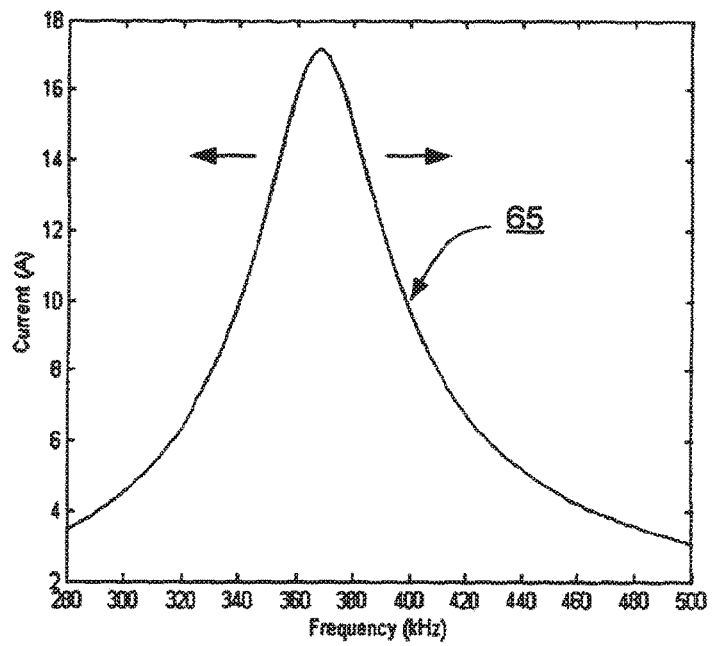
FIG. 6 is a plot illustrating the way in which the resonant characteristics of the RF drive circuit illustrated in FIG. 2 varies with different loads.

As those skilled in the art will appreciate, the resonant circuit 28 is coupled to a load 39 whose impedance will vary during the surgical procedure. Indeed the medical device control module 57 uses this variation to determine whether the tissue or vessel has been cauterised, coagulated/desiccated. The varying impedance of the load 39 changes the frequency characteristic of the RF drive circuit 20 and hence the current that flows through the resonant circuit 28. This is illustrated in FIG. 6, which is a plot 65 illustrating the way in which the current through the resonant circuit 28 varies with the drive frequency for a fixed value of load impedance. As the impedance of the load 39 increases, the resonant characteristic 65 will change shape (the peak may grow or reduce in height) and will move to the left and as the impedance of the load decreases it will change its shape and move to the right. Therefore, the frequency control module 55 must operate quickly enough to track the changes in the resonant characteristic 65. This is easily achievable in this embodiment, where power, current and voltage measurements are available every 0.01 ms. In general terms, measurements would only be required at a rate of about once every 0.1 s to track the changes. However sudden changes in the resonant characteristic 65 can occur, which the frequency control module 55 cannot track. When this happens, the frequency control module 55 resets the operating frequency to a value where it knows that it will be on one side of the characteristic.

As the impedance of the resonant circuit 28 increases sharply both above and below resonance, it is possible to operate the RF drive circuit 20 either above or below the resonant frequency. In this embodiment, the frequency control module 55 controls the operation of the drive circuit 20 so that it operates slightly above the resonant frequency as this should lead to lower switching losses through the FETs 23.

Figure 7:
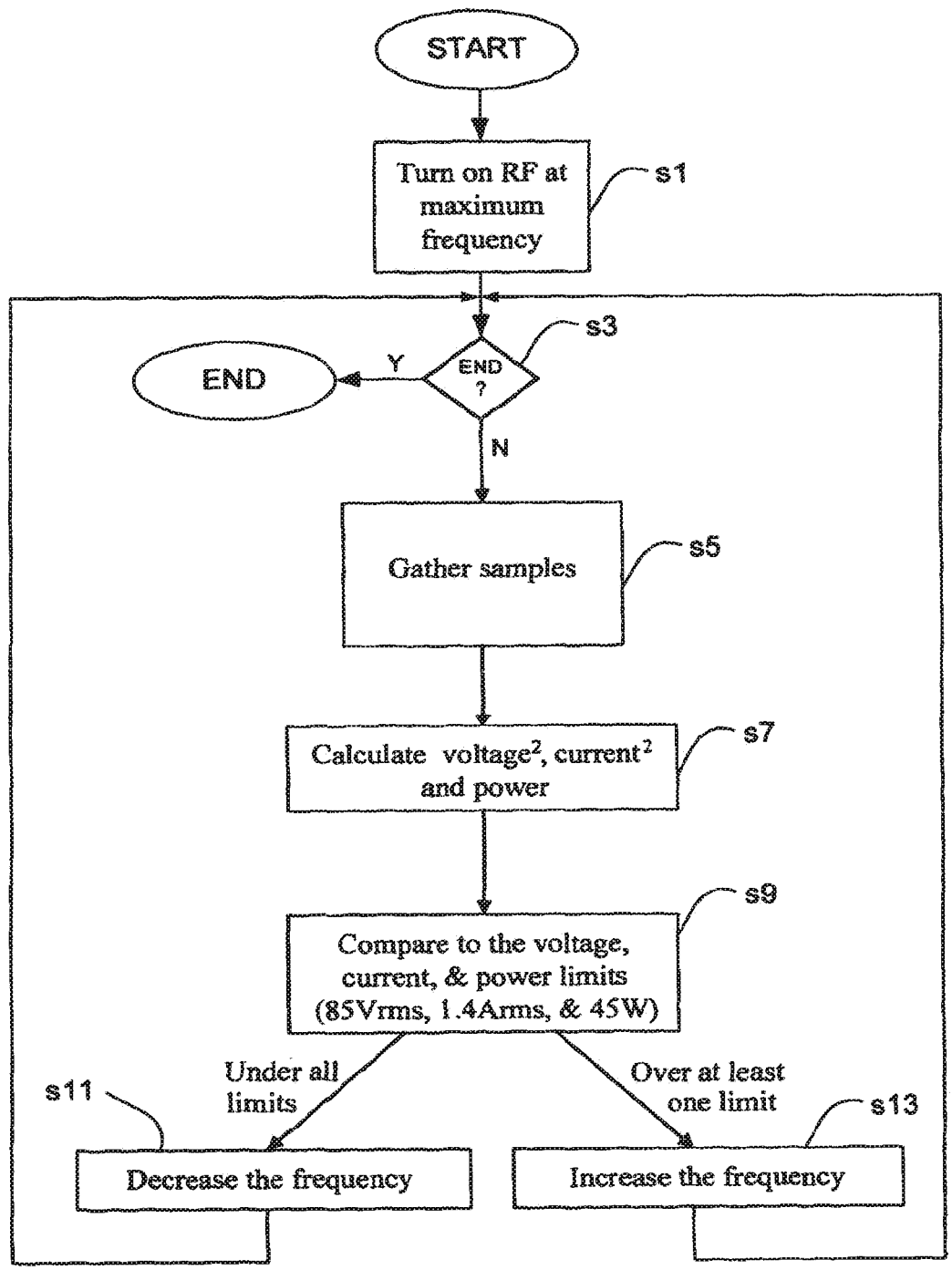
FIG. 7 is a flow chart illustrating the operation of a frequency control algorithm used to control the frequency of the RF drive signals applied to the cauterization device.

FIG. 7 illustrates the processing performed in this embodiment by the calculation module 53 and the frequency control module 55. As shown, at the beginning of the process in step s1, the control module 55 turns on the RF drive signal at the system defined maximum frequency by passing an initialisation signal to the square wave generation module 63. Provided the control module 55 has not received, in step s3, a power down signal from the medical device control module 57, the processing proceeds to step s5 where the calculation module 53 obtains the voltage and current samples from the synchronous sampling circuitry 51. In step s7 the calculation module 53 calculates the square of the voltage and the square of the current and the delivered power by multiplying the measured voltage by the measured current. These calculated values are then passed to the frequency control module 55 which compares, in step s9, the values with the defined limits for the applied voltage, current and power. The voltage and current limits are static limits that are defined in advance. However, the power limit depends on the medical procedure and is defined by the power set point ($P_{set}$) provided by the medical device control module 57. If each of the measured values is below the corresponding limit then, in step s11, the frequency control module 55 decides to decrease the drive frequency and a decrease command is passed to the square wave generator

63. At the start of the processing, the drive frequency is set to a defined maximum value (in this embodiment 500 kHz), which will always be above the resonant peak of the characteristic 65, regardless of the load impedance. Therefore, regardless of the load 39, the initial operating frequency should be on the right hand side of the resonant plot shown in FIG. 6. By decreasing the drive frequency, the drive frequency will get closer to the resonant frequency of the resonant circuit 28. As a result, the applied current will increase and more power will be delivered to the load 39. The processing then returns to step s3 and the above process is repeated.

Therefore, the current and power applied to the load 39 should increase until one of the limits is reached. At this point, the control module 55 will determine, in step s9, that a limit has been reached and so will proceed to step s13, where the control module 55 decides to increase the drive frequency and sends the square wave generation module 63 an increase command. This will cause the drive frequency to move away from the resonant frequency of the circuit 28 and so the current and power delivered to the load 39 will reduce. The processing will then return to step s3 as before.

Thus, by starting on one side of the resonant peak and slowly moving the drive frequency towards and away from the resonant peak, the current and power level applied to the load 39 can be controlled within the defined limits even as the impedance of the load changes and the resonant characteristic 65 of the resonant circuit 28 changes as the tissue/vessel is cauterised.

As those skilled in the art will appreciate, it would also be possible to start on the left hand side of the resonant peak and increase the drive frequency to increase the delivered power and decrease the drive frequency to decrease the delivered power.

Medical Device Control Module

Figure 8:
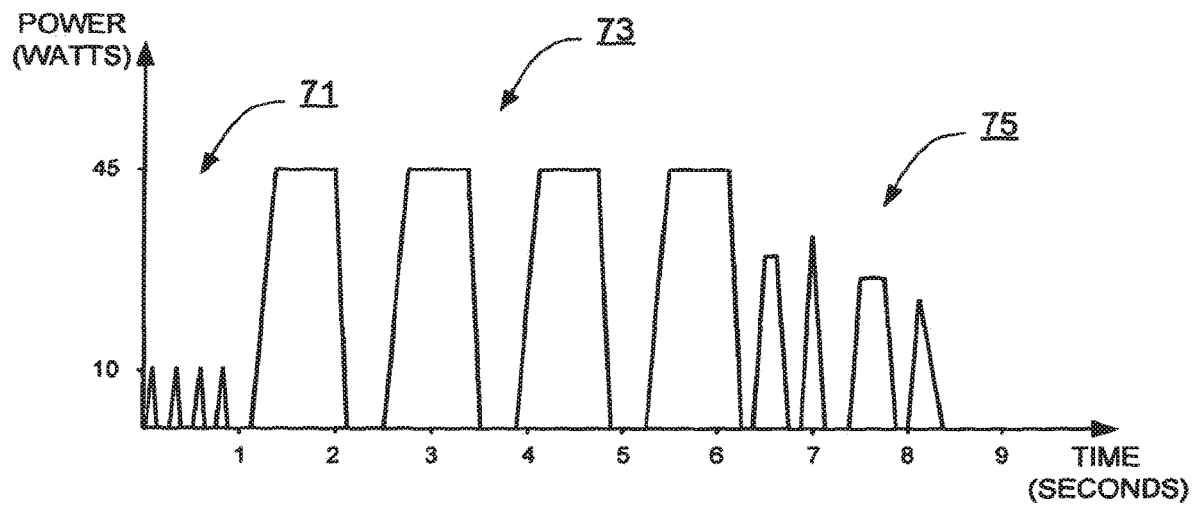
FIG. 8 is a plot illustrating one way in which the power limit can be varied by the control electronics during a surgical procedure.

As mentioned above, the medical device control module 57 controls the general operation of the cauterisation device 1. It receives user inputs via the user input module 59. These inputs may specify that the jaws of the forceps 9 are now gripping a vessel or tissue and that the user wishes to begin cauterisation. In response, in this embodiment, the medical device control module 57 initiates a cauterisation control procedure. Initially, the medical device control module 57 sends an initiation signal to the frequency control module 55 and obtains current and power measurements from the calculation module 53. The medical device control module 57 then checks the obtained values to make sure that the load 39 is not open circuit or short circuit. If it is not, then the medical device control module 57 starts to vary the power set point to perform the desired cauterisation. FIG. 8 is a plot illustrating the way in which the medical device control module 57 may vary the set point power to achieve the desired cauterisation procedure. Various other techniques and other power delivery algorithms may also be used.

As shown in FIG. 8, during an initial period 71 the medical device control module 57 pulses the set point power between zero and about 10 Watts. Then during a main cauterisation period 73 (which typically lasts for about 5 seconds) the medical device control module 57 pulses the set point power between zero and 50 Watts. During this period, the medical control device receives the power and voltage measurements from the calculation module 53 and calculates from them the impedance of the load 39. The medical device control module 57 determines that the cauterisation is complete when the calculated impedance exceeds a threshold. Finally, the medical device control module 57 performs a terminating procedure during a terminating period 75. During the terminating procedure, the medical device control module 57 varies the set point power and checks that cauterisation has been achieved (by checking the Impedance of the load using the measured power and current values) and re-enters the main cauterisation period again if it determines that cauterisation has not been completed.

Resonant Circuit Design

The way that the values of the inductors and capacitors were chosen in this embodiment will now be described. As those skilled in the art will appreciate, other design methodologies may be used.

The complex impedance of the circuit shown in FIG. 2 can be approximated by the following equation:

$$Z = j2\pi f L_s + \frac{1}{j2\pi f C_s} + \frac{j2\pi f L_m R_{load\_ref}}{j2\pi f L_m + R_{load\_ref}} + R_s. \tag{1}$$

Where:
$R_{load\_ref}$ is the load resistance referred to the primary (by the square of the turns ratio);
$R_s$ represents the equivalent series resistance of the inductor, transformer capacitor and switching devices.

All other component non-idealities are ignored and the transformer is considered to be ideal as a first approximation.

Assuming that $R_s$ is small, when the load is open circuit (ie $R_{load\_ref}$ is infinite) the resonant frequency can be shown to be:

$$f_{min} = \frac{1}{2\pi\sqrt{(L_s + L_m)C_s}} \tag{2}$$

Similarly, when the load is short circuit (ie $R_{load\_ref}$ is zero) the resonant frequency can be shown to be:

$$f_{max} = \frac{1}{2\pi\sqrt{L_s C_s}} \tag{3}$$

Assuming $R_s$ is small: at each frequency between $f_{min}$ and $f_{max}$ there is a value of the load, $R_{load}$, at which the greatest power can be dissipated in the load. This maximum power can be shown to be large at frequencies near $f_{min}$ and $f_{max}$, and has a minimum at the critical frequency, fc. We refer to this power as $P_{max\_fc}$. Starting with (1) it can be shown that the following relationship holds:

$$L_m = \frac{2V_s^2}{2\pi f_c P_{max\_fc}} \tag{4}$$

where $V_s$ is the supply voltage.

It can be shown that the load at which equation (4) holds is given by:

$$R_{load\_ref} = 2\pi f L_m \tag{5}$$

Furthermore from (1) a relationship between $f_{min}$, $f_c$ and $f_{max}$ can be established:

$$f_{min} = \sqrt{(2\pi f_c)^2 \frac{(2\pi f_{max})^2 + (2\pi f_c)^2}{3(2\pi f_{max})^2 - (2\pi f_c)^2}} \tag{6}$$

From (6) it can be shown that $f_{min} < f_c < f_{max}$. If the circuit is to operate at $f_c$, then equation (4) gives an upper bound on the worst-case power delivered across a range of loads.

From (1), it can be shown that the efficiency of the circuit at resonance may be written as:

$$\eta = \frac{\left(\frac{(2\pi f_c)^2 L_m^2 R_{load}}{(2\pi f_c)^2 L_m^2 + R_{load}^2}\right)}{Re(Z)} = \quad (7)$$

$$\frac{(2\pi f_c)^2 L_m^2 R_{load\_ref}}{R_s((2\pi f_c)^2 L_m^2 + R_{load\_ref}^2) + (2\pi f_c)^2 L_m^2 R_{load\_ref}}$$

From (7) it may be shown that the efficiency is a maximum when $R_{load\_ref} = 2\pi f L_m$, i.e. when (5) holds. Therefore the system is designed to operate around the point of maximum efficiency.

Design Procedure

For this specific embodiment of the design the following parameters were chosen:

Battery voltage of 24V however battery voltage droops with discharge and load so $V_{s\_sq}$=18V (square wave peak to peak voltage) was used $R_{load}$=45 W (maximum power into the load)

$V_{load}$=85 Vrms (maximum voltage into the load)

$I_{load}$=1.4 Arms (maximum current into the load)

$f_c$=430 kHz (centre or critical switching frequency)

$f_{max}$=500 kHz (maximum switching frequency, which is the upper resonant frequency)

$f_{min}$=380 kHz (approximate minimum switching frequency—needs to be calculated)

Given these values, $f_{min}$ can be computed using (6):

$$f_{min} = \sqrt{(2\pi 430k)^2 \frac{(2\pi 500k)^2 + (2\pi 430k)^2}{3(2\pi 500k)^2 - (2\pi 430k)^2}}$$

$$f_{min} = 377 \text{ kHz}$$

Resonant circuits produce sinusoidal waveforms therefore the input square wave voltage ($V_{s\_sq}$) needs to be converted into the RMS of the fundamental switching frequency ($V_s$).

$$V_s = \frac{4}{\pi} \frac{V_{s\_sq}}{2\sqrt{2}}$$

$$= \frac{4}{\pi} \frac{18 \text{ V}}{2\sqrt{2}}$$

$$= 8.1 \text{ V}_{rms}$$

The power into the load ($P_{load}$) is set by $L_m$. Using (4) the transformer magnetising inductance ($L_m$) can be determined. This ensures that at the critical frequency, $f_c$, the required power is delivered:

$$L_m = \frac{2V_s^2}{2\pi f_c P_{load}}$$

$$= \frac{2 \times 8.1 \text{ V}_{rms}^2}{2\pi \times 420 \text{ kHz} \times 45 \text{ W}}$$

$$= 1.08 \text{ μH}.$$

$L_s$ can then be calculated (derived from equations 2 & 3):

$$L_s = \frac{L_m}{\frac{f_{max}^2}{f_{min}^2} - 1}$$

$$= \frac{1.08 \text{ μH}}{\frac{500 \text{ kHz}}{377 \text{ kHz}} - 1}$$

$$= 1.43 \text{ μH}$$

Following from this $C_s$ can be calculated (from equation 3):

$$C_s = \frac{1}{L_s(2\pi f_{max})^2}$$

$$= \frac{1}{1.43 \text{ uH } (2\pi 500 \text{ kHz})^2}$$

$$= 71 \text{ nF}$$

To maintain regulation, the circuit is run above resonance so actual values of $C_s$ will be typically 20% higher to bring the operating point back down (if below resonance was chosen $C_s$ would have to be reduced).

As previously mentioned, the efficiency is maximised when $R_{load\_ref}$ is equal to the magnetising reactance at the critical frequency (equation 5). It is desirable, therefore, to operate about the middle of the constant power range (shown in FIG. 5b). $R_{load\_upper}$ is the load resistance at which constant power changes to constant voltage. Similarly, $R_{load\_lower}$ is the load resistance at which constant power changes to constant current.

$$R_{load\_upper} = \frac{V_{load}^2}{P}$$

$$= \frac{85 \text{ V}_{rms}^2}{45 \text{ W}}$$

$$= 161 \text{ Ω}$$

$$R_{load\_lower} = \frac{P}{I_{load}^2}$$

$$= \frac{45 \text{ W}}{1.4 \text{ A}^2}$$

$$= 23 \text{ Ω}$$

Take the geometric mean of these load resistances to find $R_{load\_c}$ (centre or critical load resistance)

$$R_{load\_c} = \sqrt{R_{load\_upper} R_{load\_lower}}$$

$$= 60 \text{ Ω}$$

As discussed, for maximum efficiency, $R_{load\_ref}$ should match the impedance of the primary-referred magnetising reactance at $f_c$. Hence $R_{load}$ should equal the secondary-referred magnetising reactance. $L_{sec}$ can therefore be calculated as follows:

$$L_{sec} = \frac{R_{load\_c}}{2\pi f_c}$$

$$= \frac{60}{2\pi 430 \text{ kHz}}$$

$$= 22.2 \text{ μH}$$

Finally the transformer turns ratio can be calculated:

$$N = \sqrt{\frac{L_{sec}}{L_m}}$$

$$= \sqrt{\frac{22.2 \text{ μH}}{1.08 \text{ μH}}}$$

$$= 4.5$$

For any particular design it may be necessary to adjust the values due to the following reasons:
- to maximise efficiency
- compensate non ideal effect of components (e.g. series resistance, parasitic capacitance & inductance, non ideal transformer characteristics such as leakage inductance)
- make the design practical (e.g. use standard values of capacitors and a whole number of turns
- allow margin to meet the requirements due to component tolerances, temperature etc In this specific embodiment, the component values were optimised to:
Cs=82 nF
Lm=1.1 uH
Ls=1.4 uH
N=5 which gives Lsec=24 uH The following subsections briefly describe how these component values were physically implemented.

Capacitor Selection

A low loss capacitor is desired to minimise losses and to ensure the component doesn't get too hot. Ceramic capacitors are ideal and the dielectric type of COG/NPO were used in this embodiment. The capacitor voltage rating is also important as it shouldn't be exceeded under all load conditions. Ten 250V 8.2 nF 1206 COG/NPO ceramics capacitors in parallel were used in this embodiment.

Inductor and Transformer

In this embodiment, Ferroxcube 3F3 E3216/20 e-core/plate combination was used as a ferrite core. Ferroxcube 3F3 is supplied by Ferroxcube, a subsidiary of Yageo Corporation, Taiwan. It is a high frequency ferrite material optimised for frequencies between 200 kHz and 500 kHz. By using this material the core losses are minimised. Core losses increase strongly with increasing flux density. In an inductor, for a particular required energy storage, the flux density increases with decreasing air gap (the air gap is the separation between the e-core & plate). Therefore the air gap and the number of turns can be increased to decrease core losses but this has to be balanced with the actual inductance value required and increased resistive losses introduced with the longer wire/track length.

The same issues apply to the transformer except core losses are due to the output voltage and the number of turns. Since the output voltage is fixed the number of turns is the only variable that can be changed but again this has to be balanced with resistive losses. Once the number of turns is set the air gap can then be adjusted to set Lm. Whatever core is used, it is best practise to fill the winding space with as much copper as possible to minimise resistive losses. In the transformer the volume of windings is preferably about the same in the primary and secondary to balance the losses.

The resistive losses can usually be easily calculated but since the circuit is operating at about 400 kHz skin depth becomes an issue. The skin depth in copper at 400 kHz is only about 0.1 mm so a solid conductor thicker than this doesn't result in all the copper being used. Litz wire (stranded insulated copper wire twisted together where each strand is thinner than the skin depth) can be used to reduce this effect. In this embodiment 2 oz PCB tracks (about 0.07 mm thick copper tracks) were used for the windings of both the inductor ($L_s$) and the transformer to avoid having to wind custom components. The inductor had two turns with an air gap of 0.5 mm between the e-core and plate. The transformer had one turn on the primary and five turns on the secondary with an air gap between the e-core and plate of 0.1 mm.

MODIFICATIONS AND ALTERNATIVES

A medical cauterisation device has been described above. As those skilled in the art will appreciate, various modifications can be made and some of these will now be described. Other modifications will be apparent to those skilled in the art.

In the above embodiment, various operating frequencies, currents, voltages etc were described. As those skilled in the art will appreciate, the exact currents, voltages, frequencies, capacitor values, inductor values etc. can all be varied depending on the application and the values described above should not be considered as limiting in any way. However, in general terms, the circuit described above has been designed to provide an RF drive signal to a medical device, where the delivered power is desired to be at least 10 W and preferably between 10 W and 200 W; the delivered voltage is desired to be at least 20 $V_{rms}$ and preferably between 30 $V_{rms}$ and 120 $V_{rms}$; the delivered current is designed to be at least 0.5 $A_{rms}$ and preferably between 1 $A_{rms}$ and 2 $A_{rms}$; and the drive frequency is at least 50 kHz.

Figure 9:
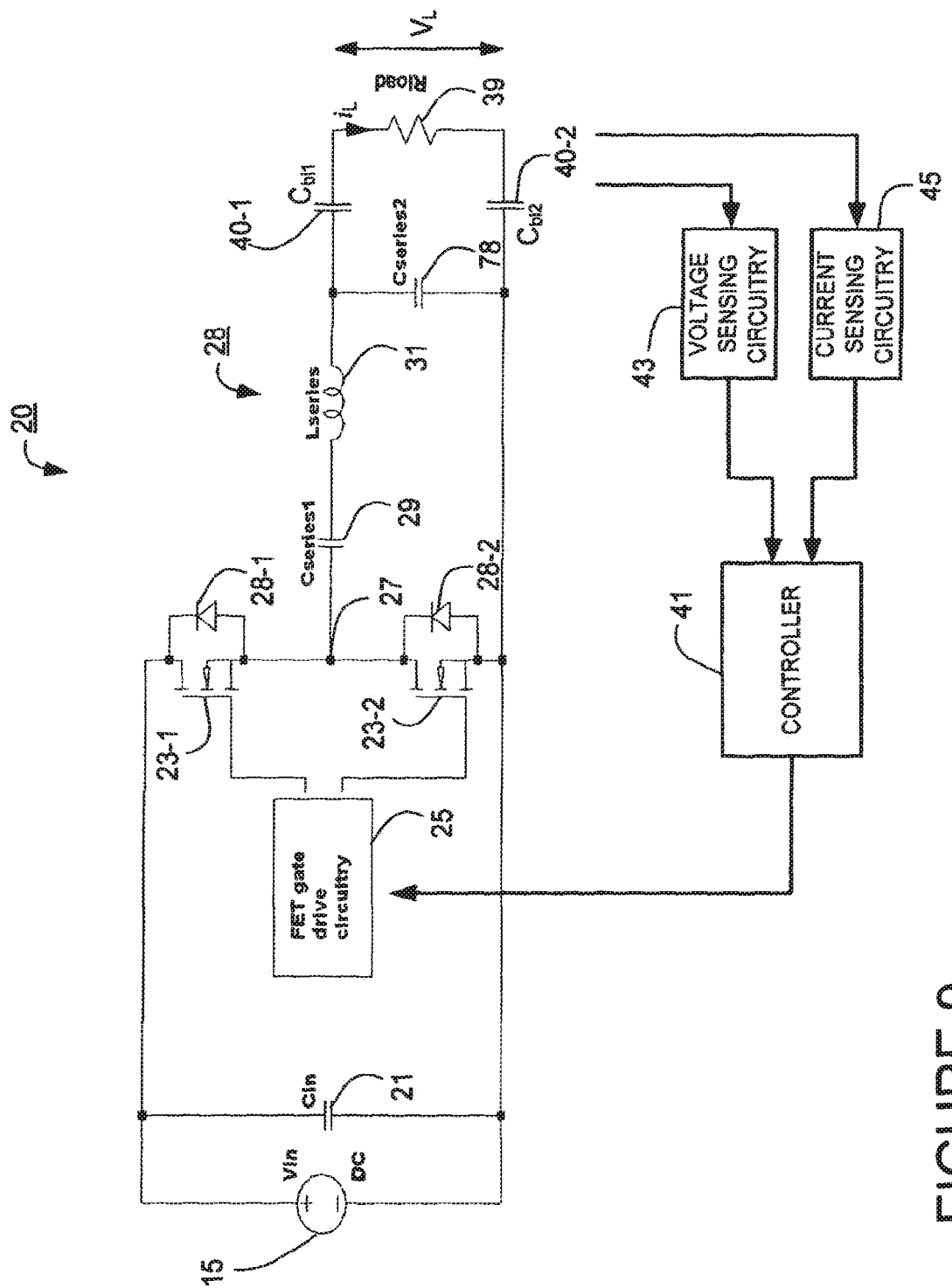
FIG. 9 is a part block part schematic diagram illustrating the main components of another RF drive circuit and control circuit embodying the invention.
Figure 10:
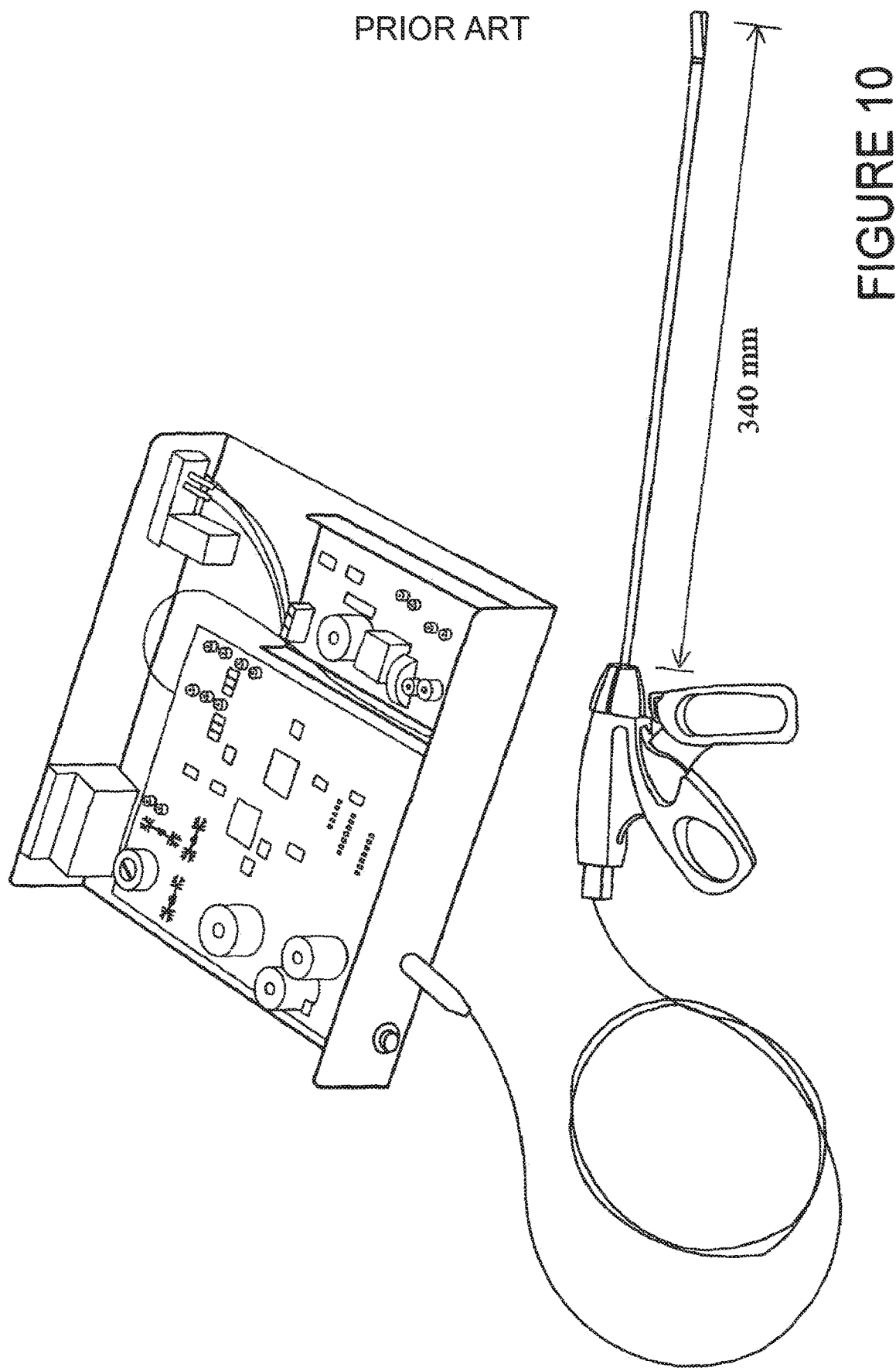
FIG. 10 illustrates the form of a prior art hand-held cauterization device which is connected to power supply and control electronics via a power supply line.
Figure 11:
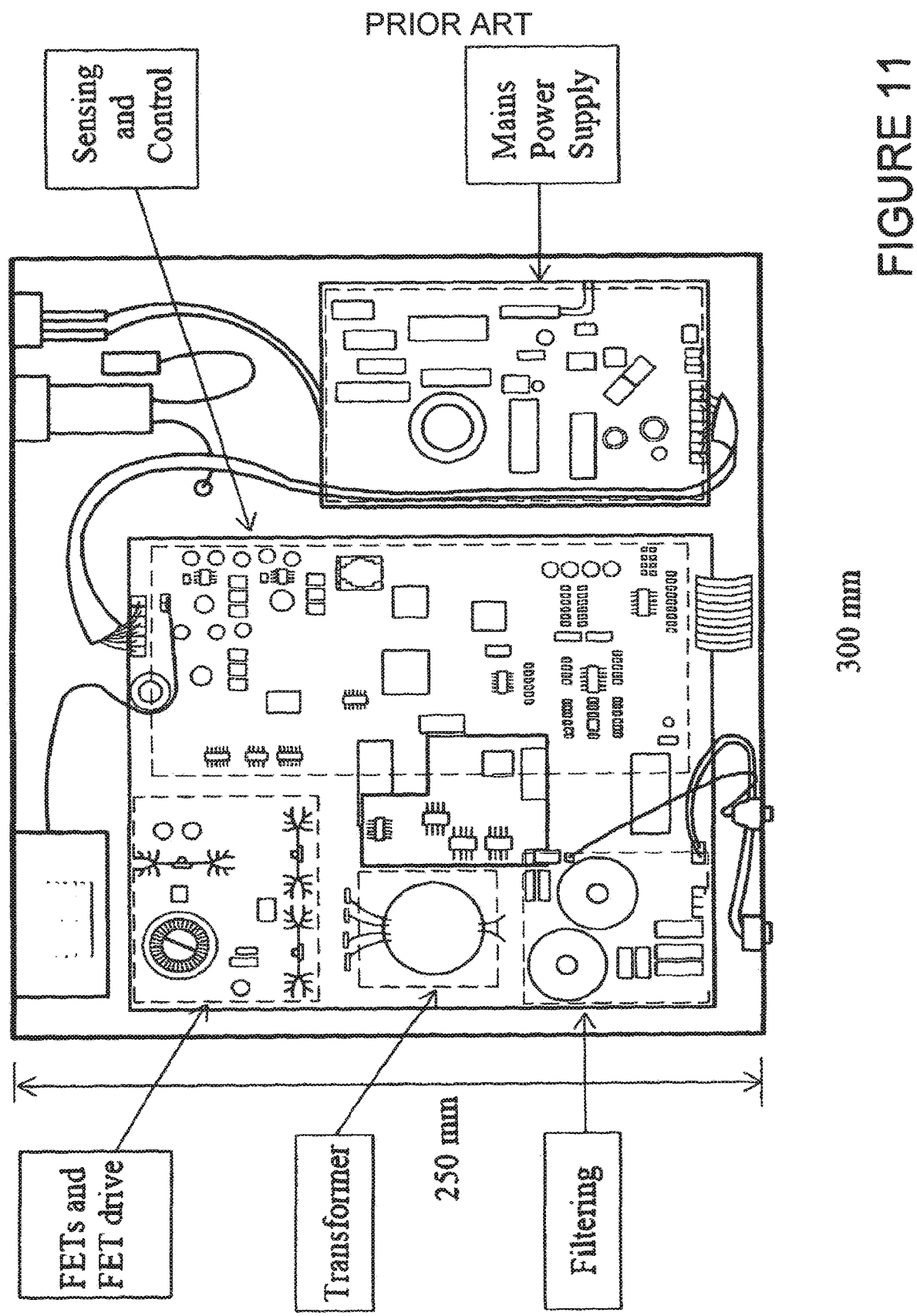
FIG. 11 is a plan view illustrating the different components of the existing electronics used to drive and control the hand-held cauterization device illustrated in FIG. 10.

In the above embodiment, the resonant circuit 28 was formed from capacitor-inductor-inductor elements. As those skilled in the art will appreciate, the resonant circuit 28 can be formed from various circuit designs. FIG. 9 illustrates another resonant circuit design that can be used in other embodiments. In the design shown in FIG. 9, the resonant circuit 28 is formed from capacitor-inductor-capacitor elements, with the load being connected across the second capacitor 78. As shown, in this design, there is no transformer and so there is no step-up in voltage. However, the operation of this embodiment would still be the same as in the embodiment described above and so a further description shall be omitted. Other resonant circuit designs with multiple capacitors and inductors in various series and parallel configurations or simpler LC resonant circuits may also be used.

FIG. 1 illustrates one way in which the batteries and the control electronics can be mounted within the handle of the medical device. As those skilled in the art will appreciate, the form factor of the handle may take many different designs.

In the above embodiment, an exemplary control algorithm for performing the cauterisation of the vessel or tissue gripped by the forceps was described. As those skilled in the art will appreciate, various different procedures may be used and the reader is referred to the literature describing the operation of cauterisation devices for further details.

In the above embodiment, the RF drive signal generated by the drive circuitry was directly applied to the two forceps jaws of the medical device. In an alternative embodiment, the drive signal may be applied to one jaw, with the return or ground plane being provided through a separate connection on the tissue or vessel to be cauterised.

In the above embodiments, the forceps jaws were used as the electrodes of the medical device. In an alternative device, the electrodes may be provided separately from the jaws.

In the above embodiments, two FET switches were used to convert the DC voltage provided by the batteries into an alternating signal at the desired RF frequency. As those skilled in the art will appreciate, it is not necessary to use two switches—one switch may be used instead or multiple switches may be used connected, for example, in a bridge configuration. Additionally, although FET switches were used, other switching devices, such as bipolar switches may be used instead. However, MOSFETs are preferred due to their superior performance in terms of low losses when operating at the above described frequencies and current levels.

In the above embodiment, the resonant circuit 28 acted as a frequency dependent attenuator. The resonant circuit was designed as a substantially lossless attenuator, but this is not essential. The resonant circuit may include lossy components as well, although the resulting circuit will of course be less efficient.

In the above embodiment, the I & Q sampling circuitry 51 sampled the sensed voltage/current signal once every period and combined samples from adjacent periods. As those skilled in the art will appreciate, this is not essential. Because of the synchronous nature of the sampling, samples may be taken more than once per period or once every $n^{th}$ period if desired. The sampling rate used in the above embodiment was chosen to maximise the rate at which measurements were made available to the medical device control module 57 as this allows for better control of the applied power during the cauterisation process.

In the above embodiment, a 24V DC supply was provided. In other embodiments, lower DC voltage sources may be provided. In this case, a larger transformer turns ratio may be provided to increase the load voltage to a desired level or lower operating voltages may be used.

In the above embodiment, a synchronous sampling technique was used to obtain measurements of the load voltage and load current. As those skilled in the art will appreciate, this is not essential and other more conventional sampling techniques can be used instead.

In the above embodiment, the medical device was arranged to deliver a desired power to the electrodes of the end effector. In an alternative embodiment, the device may be arranged to deliver a desired current or voltage level to the electrodes of the end effector.

In the above embodiment the battery is shown integral to the medical device. In an alternative embodiment the battery may be packaged so as to clip on a belt on the surgeon or simply be placed on the Mayo stand. In this embodiment a relatively small two conductor cable would connect the battery pack to the medical device.

The invention claimed is:

1. A method of operating a medical device comprising generating a radio frequency (RF) signal and applying the RF signal to at least one electrode of an end effector of the medical device and controlling a frequency of the generated RF signal to control at least one of a power, a current, and a voltage applied to the at least one electrode, wherein the power applied to the at least one electrode is controlled by varying the frequency of the generated RF signal toward and away from a resonant frequency of a resonant circuit coupled to the at least one electrode, wherein as the frequency is varied toward the resonant frequency the power applied to the at least one electrode is less attenuated and as the frequency is varied away from the resonant frequency the power applied to the at least one electrode is more attenuated.

2. A method of cauterizing a vessel or tissue, the method comprising:
   gripping the vessel or tissue with an end effector of a medical device;
   applying an RF signal to at least one electrode of the end effector that is in contact with the vessel or tissue; and
   controlling a frequency of the RF signal to control at least one of a power, a current, and a voltage applied to the vessel or tissue to perform the cauterizing, wherein the power applied to the at least one electrode is controlled by varying the frequency of the RF signal toward and away from a resonant frequency of a resonant circuit coupled to the at least one electrode, wherein as the frequency is varied toward the resonant frequency the power applied to the at least one electrode is less attenuated and as the frequency is varied away from the resonant frequency the power applied to the at least one electrode is more attenuated.

3. The method according to claim 2, which uses the medical device comprising:
   a handle for gripping by a user, the end effector coupled to the handle and having the at least one electrode;
   a radio frequency (RF) generation circuit coupled to the handle and operable to generate the RF signal and to provide the RF signal to the at least one electrode;
   wherein the RF generation circuit comprises the resonant circuit.

4. The method according to claim 2, wherein controlling the frequency comprises:
   varying the frequency of the RF signal to control the power applied to the tissue or vessel;
   obtaining measurements of an impedance of the tissue or vessel; and
   varying the power applied to the tissue or vessel in dependence upon the obtained impedance measurements.

* * * * *